(12) United States Patent
Vol et al.

(10) Patent No.: US 9,504,648 B2
(45) Date of Patent: *Nov. 29, 2016

(54) MATRIX CARRIER COMPOSITIONS, METHODS AND USES

(71) Applicant: OSHADI DRUG ADMINISTRATION LTD., Rehovot (IL)

(72) Inventors: Alexander Vol, Rehovot (IL); Orna Gribova, Rehovot (IL)

(73) Assignee: Oshadi Drug Administration Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,585

(22) Filed: May 18, 2015

(65) Prior Publication Data

US 2015/0245993 A1    Sep. 3, 2015

Related U.S. Application Data

(63) Continuation of application No. 13/381,225, filed as application No. PCT/IL2010/000551 on Jul. 8, 2010, now Pat. No. 9,060,932.

(60) Provisional application No. 61/224,100, filed on Jul. 9, 2009.

(51) Int. Cl.
*A61K 9/00* (2006.01)
*A61K 9/107* (2006.01)
(Continued)

(52) U.S. Cl.
CPC ............. *A61K 9/006* (2013.01); *A61K 9/0019* (2013.01); *A61K 9/0095* (2013.01); *A61K 9/10* (2013.01); *A61K 9/107* (2013.01); *A61K 47/02* (2013.01); *A61K 47/26* (2013.01)

(58) Field of Classification Search
CPC .... A61K 47/02; A61K 47/26; A61K 9/0019; A61K 9/006; A61K 9/0095; A61K 9/10; A61K 9/107
See application file for complete search history.

(56) References Cited

U.S. PATENT DOCUMENTS 3,252,859 A    5/1966   Silver
5,145,684 A    9/1992   Liversidge
(Continued)

FOREIGN PATENT DOCUMENTS

EP    0491114    6/1992
EP    1179349    2/2002
(Continued)

OTHER PUBLICATIONS

Bjork et al., (1995) Starch Microspheres Induce Pulsatile Delivery of Drugs and Peptides Across the Epithelial Barrier by Reversible Separation of the Tight Junctions. J Drug target 2(6): 501-507.
Chung et al., Hydrophobic modification of silica nanoparticle by using aerosol spray reactor. Colloids and Surfaces A: Physicochem. Eng. Aspects 2004; 236:73-9.
(Continued)

*Primary Examiner* — Aradhana Sasan
(74) *Attorney, Agent, or Firm* — Rodney J. Fuller; Booth Udall Fuller, PLC

(57) ABSTRACT

Provided is a matrix carrier composition for use in pharmaceutical delivery system, the composition comprising an intermolecular association of at least a first solid phase comprising nanoparticles having hydrophobic surface, wherein the size of the nanoparticles is in the range of about 5-1000 nm, a second solid phase, comprising a biopolymer having hydrophilic and hydrophobic parts, and a continuous phase comprising oil associated with the first and said second solid phases.

19 Claims, 2 Drawing Sheets

(51) Int. Cl.
   *A61K 47/26* (2006.01)
   *A61K 9/10* (2006.01)
   *A61K 47/02* (2006.01)

(56) References Cited

U.S. PATENT DOCUMENTS

| | | | |
|---|---|---|---|
| 5,462,866 | A | 10/1995 | Wang |
| 5,843,509 | A | 12/1998 | Calvo Salve |
| 5,874,105 | A | 2/1999 | Watkins |
| 6,071,535 | A | 6/2000 | Hayward |
| 6,228,377 | B1 | 5/2001 | Sebillotte-Arnaud |
| 6,322,765 | B1 | 11/2001 | Muehlhofer |
| 6,458,387 | B1 | 10/2002 | Scott |
| 6,482,517 | B1 | 11/2002 | Anderson |
| 6,528,497 | B1 | 3/2003 | Basten |
| 6,548,264 | B1 | 4/2003 | Tan |
| 6,551,576 | B1 | 4/2003 | Unger |
| 6,638,621 | B2 | 10/2003 | Anderson |
| 6,656,922 | B2 | 12/2003 | Byun |
| 6,667,060 | B1 | 12/2003 | Vandecruys |
| 6,698,247 | B2 | 3/2004 | Tennent |
| 6,808,720 | B2 | 10/2004 | Unger |
| 6,989,195 | B2 | 1/2006 | Anderson |
| 7,045,146 | B2 | 5/2006 | Caruso |
| 7,083,572 | B2 | 8/2006 | Unger |
| 7,090,868 | B2 | 8/2006 | Gower |
| 7,105,229 | B2 | 9/2006 | Anderson |
| 7,195,780 | B2 | 3/2007 | Dennis |
| 7,316,818 | B2 | 1/2008 | Yatvin |
| 7,351,741 | B2 | 4/2008 | Weidner |
| 7,384,914 | B2 | 6/2008 | Goldberg |
| 7,455,830 | B2 | 11/2008 | Sung |
| 7,470,663 | B2 | 12/2008 | Ekwuribe |
| 7,718,609 | B2 | 5/2010 | Steiner |
| 8,936,786 | B2 * | 1/2015 | Vol ............ A61K 38/23 424/178.1 |
| 9,060,932 | B2 * | 6/2015 | Vol ............ A61K 9/0095 |
| 2002/0150621 | A1 | 10/2002 | Kohane |
| 2003/0035888 | A1 | 2/2003 | Eriyama |
| 2003/0235619 | A1 | 12/2003 | Allen |
| 2004/0091541 | A1 | 5/2004 | Unger |
| 2004/0115264 | A1 | 6/2004 | Blouquin |
| 2004/0242729 | A1 | 12/2004 | Baran |
| 2005/0170004 | A1 | 8/2005 | Rosenberger |
| 2006/0053971 | A1 | 3/2006 | Sun |
| 2006/0083781 | A1 | 4/2006 | Shastri |
| 2006/0177495 | A1 | 8/2006 | Allen |
| 2006/0204559 | A1 | 9/2006 | Bess |
| 2006/0234913 | A1 | 10/2006 | Arbit |
| 2007/0098990 | A1 | 5/2007 | Cook |
| 2007/0104778 | A1 | 5/2007 | Zeng |
| 2007/0134332 | A1 | 6/2007 | Turnell |
| 2007/0154559 | A1 | 7/2007 | Pai |
| 2007/0172426 | A1 | 7/2007 | Lee |
| 2007/0184076 | A1 | 8/2007 | Unger |
| 2007/0196656 | A1 | 8/2007 | Rowell |
| 2007/0258889 | A1 | 11/2007 | Douglas |
| 2007/0275969 | A1 | 11/2007 | Gurny |
| 2010/0278922 | A1 | 11/2010 | Vol |
| 2010/0297245 | A1 | 11/2010 | Vol |

FOREIGN PATENT DOCUMENTS

| | | |
|---|---|---|
| WO | 96/37232 | 11/1996 |
| WO | 03/066859 | 8/2003 |
| WO | 2005/094785 | 10/2005 |
| WO | 2006/062544 | 6/2006 |
| WO | 2006/097793 | 9/2006 |
| WO | 2009/087634 | 7/2009 |

OTHER PUBLICATIONS

Durand et al., (2004) Amphiphilic polysaccharides: useful tools for the preparation of nanoparticles with controlled surface characteristics. Langmuir 20: 6956-63.

Eleftheriadou et al., (2008) The effects of medications used for the management of diabetes and obesity on postprandial lipid metabolism. Curr Diabetes Rev 4(4): 340-56.

Entries for "association" and "intimate" as retrieved from www.dictionary.com on Jul. 11, 2012 pp. 1-6.

Fu et.al., (2001) Synthesis of titania-coated silica nanoparticles using a nonionic water-in-oil microemulsion. Colloids and Surfaces A: Physicochem. Eng Aspects 179: 65-70.

Gurkov and Basheva (2006) Hydrodynamic behavior and stability of approaching deformable drops. In: Encyclopedia of Surface and Colloid Science; Somasundaran P (editor), vol. 4, 2nd edition, CRC Press, Taylor & Francis Group, FL, USA.

Hawley's condensed chemical dictionary LEWIS, Richard J. (ed.) 15th edition., 2007 Wiley-Interscience, entry "amylopectin," p. 79.

Jean and Yang (2000) Y2O2S:Eu Red Phosphor Powders Coated with Silica Am Ceram Soc 83(8): 1928-34.

Krysztafkiewicz et.al., (2000) Precipitated silicas modified with 3-aminopropyltriethoxysilane. Colloids Surf. A: Physicochem. Eng Aspects 173: 73-84.

Lewis, Richard J.: "Hawley's Condensed Chemical Dictionary", 2007, p. 1174.

Li and Deng (2004) Oil-based formulations for oral delivery of insulin. J Pharm Pharmacol 56(9): 1101-1107.

Lin et al., (2007) Preparation and characterization of nanoparticles shelled with chitosan for oral insulin delivery. Biomacromolecules 8(1): 146-52.

Lincopan et al., (2009) Silica-based cationic bilayers as immunoadjuvants. BMC Biotechnol 9: 5.

Merriam-Webster's Collegiate Dictionary, 11th edition, 2003 Merriam-Websters Inc; entry for derivatives pp. 1-20.

Nadano et al., (1993) Measurement of deoxyribonuclease I activity in human tissues and body fluids by a single radial enzyme-diffusion method. Clinical Chemistry 39: 448-52.

Okada et al., (1983) Chemical Synthesis of Polysaccharides III. A Synthetic Polysaccharide Having One Hydroxyl Group in Its Repeating Unit, 3,4-Dideoxy-(1 6)-α-dl-threo-hexopyranan. Polymer Journal 15(11): 821-26.

Ou et al., (2003) L-4F, an apolipoprotein A-1 mimetic, dramatically improves vasodilation in hypercholesterolemia and sickle cell disease. Circulation 107: 2337-41.

Schipper et al., (1997) Chitosans as absorption enhancers for poorly absorbable drugs 2: mechanism of absorption enhancement. Pharm Res 14(7): 923-929.

Sihorkar and Vyas (2001) Potential of polysaccharide anchored liposomes in drug delivery, targeting and immunization. J Pharm Pharm Sci 4(2): 138-158.

Vaidya et al., (2008) Glucagon like peptides-1 modulators as newer target for diabetes. Curr Drug Targets 9(10): 911-20.

Varshosaz (2007) Insulin Delivery Systems for Controlling Diabetes. Recent Patents on Endocrine, Metabolic & Immune Drug Discovery 1: 25-40.

Ververidis et al., (2007) Biotechnology of flavonoids and other phenylpropanoid-derived natural products. Part I: Chemical diversity, impacts on plant biology and human health. Biothechnol J 2(10): 1214-1234.

Ververidis et al., (2007) Biotechnology of flavonoids and other phenylpropanoid-derived natural products. Part II: Reconstruction of multienzyme pathways in plants and microbes. Biothechnol J 2(10): 1235-1249.

Zhang and Gao (2001) Nanocomposite powders from coating with heterogeneous nucleation processing. Ceram Int 27: 143-7.

* cited by examiner

MATRIX CARRIER COMPOSITIONS, METHODS AND USES

RELATED APPLICATION DATA

This application is a continuation of U.S. patent application Ser. No. 13/381,225, filed Dec. 28, 2011 (published as US 20120100216), which is the U.S. National Stage of International Application No. PCT/IL2010/000551, filed Jul. 8, 2010, which claims the benefit of U.S. Provisional Patent Application No. 61/224,100, filed Jul. 9, 2009, the contents of each of which are expressly incorporated by reference in their entireties for all purposes.

FIELD OF THE INVENTION

The present invention relates to matrix carrier compositions, methods for their preparations and uses thereof, for example, in pharmaceutical delivery systems.

BACKGROUND

Oral delivery is considered to be a convenient and widely accepted route of drug administration. Achieving good oral bioavailability for drugs is a cornerstone for an effective oral therapy. The use of an effective carrier for drugs having low bioavailability enables an effective oral administration with improve drug potency and may be used for new drugs, as well as for old medicines that have not historically been available orally.

The term bioavailability with respect to oral administration of drugs is directed to the fraction of drug that has reached the systemic circulation after oral administration, while taking into account both absorption and metabolism of the drug. The bioavailability may be affected/dependent on several factors, some of which are related to the Gastrointestinal (GI) tract and some are related to the metabolism of the drug before entering the systemic circulation. The factors include, for example, such factors as: GI motility, GI pH and enzymatic composition including protease, lipase, nuclease, and the like, Particle (active drug) size, physicochemical interaction with gut content, metabolism of the drug by enzymes and electrolytes in the GI tract, metabolism during the first pass clearance of the drug (such as, for example, metabolism of the drug in the liver), Chemical characteristic of the drug (such as, for example, low lipid solubility, acidity of the drug), and the like.

With respect to protein drugs, two main factors limit their use by oral route of administration. One is the rapid degradation of the protein drugs, which occurs in GI tract by intestinal enzymes and in mucosal tissues that generally cover the body cavities. The other factor that limits the oral administration of protein drugs is that most protein drugs are relatively large molecules and therefore do not easily crosses the intestinal epithelium. As a result, the bioavailability of orally administered protein-based drugs is typically extremely low. Accordingly, the most common route of protein drugs administration is the parenteral route, which has several drawbacks, such as, for example, being inconvenient to the patients, and being more expensive in terms of drug administration. There is therefore an unmet medical need for an effective non-parenteral mode of administration of protein drugs that will provide protection against biological degradation, improve pharmacokinetics and reduce toxicity. Although sophisticated non-parenteral pharmaceutical systems, such as intra-nasal or inhaled systems, have been developed, oral administration is more favorable, having the major advantage of convenience for increased patient compliance. Various strategies for oral administration of protein drugs have been suggested, such as for example in the following publications: U.S. Pat. No. 7,090,868, U.S. Pat. No. 7,195,780, U.S. Pat. No. 7,316,818, WO 06/062544, U.S. Pat. No. 6,071,535, U.S. Pat. No. 5,874,105, U.S. Pat. No. 6,551,576, U.S. Pat. No. 6,808,720, U.S. Pat. No. 7,083,572, US 2007/0184076, WO 06/097793, WO 05/094785, WO 03/066859 and EP0491114B1.

Additionally, since bioavailability may be low for non-protein drugs there is also a growing need for the development of a drug delivery system that can protect the drug from the environment and may direct the drug to a targeted site or organ, obviating unwanted side effects while simultaneously reducing dose and toxicity, improve potency of the drug, and improve the drug's bioavailability.

SUMMARY

The following embodiments and aspects thereof are described and illustrated in conjunction with systems, tools and methods which are meant to be exemplary and illustrative, not limiting in scope.

According to some embodiments there is provided a matrix carrier composition for use in a pharmaceutical composition with a pharmaceutical agent. The matrix comprises an intermolecular association of at least a first solid phase, preferably nanoparticles with size in range 5-1000 nm having hydrophobic surface; a second solid phase, preferably a biopolymer (such as, for example, a polysaccharide) having both hydrophilic and hydrophobic parts; and a continuous phase of oil associated with all the ingredients of the matrix.

There are further provided methods for manufacturing matrix carrier compositions and methods for the use of matrix carrier compositions.

According to some embodiments, there are provided matrix carrier compositions, suitable for the delivery of a pharmaceutical agent, comprising a particulate matter comprising pharmacologically inert nanoparticles, in non-covalent association with a biopolymer and a pharmaceutical agent, wherein the particulate matter is associated with a continuous phase of oil. According to additional embodiments, there are further provided methods of manufacturing matrix carrier composition, pharmaceutical compositions comprising the same, and therapeutic methods utilizing same. In some embodiments, the delivery is oral delivery. In some embodiments, the delivery is parenteral. In some embodiments, the delivery is topical.

According to some embodiments, there is provided pharmaceutical composition, including an oil comprising particulate matter, wherein the particulate matter comprises a biopolymer in non-covalent association with silica nanoparticles having a hydrophobic surface; and a pharmaceutical agent, non-covalently associated with the silica nanoparticles and the biopolymer. According to some embodiments, there is provided a method of manufacturing a pharmaceutical composition, the method includes: mixing nanoparticles with a biopolymer, whereby the nanoparticles form a non-covalent association with the biopolymer; mixing a pharmaceutical agent with oil, and mixing the nanoparticles and biopolymer with the oil, wherein the pharmaceutical agent forms a non-covalent association with the nanoparticles and the biopolymer and wherein the inert nanoparticles, the biopolymer, and the pharmaceutical agent are associated with the oil.

According to further embodiments, the pharmaceutical composition is anhydrous.

According to further embodiments, the matrix carrier composition is preferably in the absence of water.

According to further embodiments, the matrix carrier composition is preferably in the absence of additional surfactants.

In some embodiments the inert nanoparticles include silica nanoparticles, where at least 80% of silica is hydrophobic silica.

According to further embodiments, substantially anhydrous matrix carrier pharmaceutical composition may include molecules and/or particles having hydrophilic properties. Non limiting examples are hydrophilic silica, water soluble vitamins, and the like.

According to further embodiments, the nanoparticles include silica nanoparticles, and the size of the majority of the silica nanoparticles may be between 1-1000 nanometers. According to additional embodiments, the biopolymer may include a polysaccharide, saccharide, and/or oligosaccharide. The polysaccharide may include branched and/or unbranched and/or cyclic polysaccharides, wherein the polysaccharides may include such polysaccharide as, but not limited to: nutriose, maltsorb, beta-cycelodextrin, xylitol, mannitol, fiber, amylopectin, glucan, starch, glycogen and glycosaminoglycans (GAGs), mucopolysaccharides or derivatives thereof. According to further embodiments, a branched biopolymer may be used in the pharmaceutical composition.

According to additional embodiments, the pharmaceutical composition may further include a structural protein selected from the group consisting, for example, but not limited to: elastin, collagen, keratin, and fibrinogen. The pharmaceutical composition may further include an amino acid selected from the group consisting of arginine, lysine, glutamic acid, aspartic acid and histidine. According to other embodiments, the pharmaceutical composition may further include an antioxidant.

According to other embodiments, the pharmaceutical composition may further include one or more enhancers and/or targeting agents.

According to some embodiments, the pharmaceutical composition may include more than one pharmaceutical agent and/or nutritional agent.

According to further embodiments, the process of the preparation of the matrix composition provides a formation of a complex, which includes non-covalent bonds between hydrophobic surface of the nanoparticles ("First solid phase"), biopolymers ("Second solid phase") and/or oil molecules and hydrophobic surface of the pharmaceutical agent.

According to further embodiments the process of the preparation of the matrix provides a formation of a complex, which includes additional non-covalent bonds between hydrophilic surface of the pharmaceutical agent, biopolymer ("Second solid phase") and polar groups of the oils.

According to further embodiments, the matrix carrier composition may further include hydrophilic nanoparticles and one or more additional enhancers and/or targeting agents.

According to some embodiments, the volume ratio between the volume of first solid phase and the volume of the second solid phase may be at a desired ratio so as to optimize the protecting properties of the matrix carrier. The volume ratio may be determined according to the speed of sound (c) of each solid phase. In some embodiments, the volume ratio may be determined according to equation 1:

$$V1 \times c1 \leq V2 \times c2 \qquad \text{(equation 1);}$$

wherein

V1 is the volume of the first solid phase;
c1 is the speed of sound in the first solid phase;
V2 is the volume of the second solid phase; and
c2 is the speed of sound in the second solid phase.

According to some embodiments the methods for the preparation of the matrix-carrier includes at least some of the following steps:

Activation of the second solid phase surface of matrix-carrier by additional milling, vacuum treatment, chemical or ultra-sound cleaning or reduction; mixing one or more biopolymers with liquid oils under vacuum or in inert atmosphere; Inserting nanoparticles into oils and additional vacuum treatment for removing air from the nanoparticles surface; Inserting one or more pharmaceutical agents into pure oils, oils with hydrophobic nanoparticles or oils with biopolymer with or without the silica nanoparticles, depending on the physical properties (such as, for example, hydrophobicity, sensitivity to mechanical stress) of the pharmaceutical agent; Homogenization of the system while taking into consideration the sensitivity of the active pharmaceutical to mechanical stress. The homogenization may be performed under inert atmosphere with controlled temperature, rate and time. The homogenization or mixing may aid in decreasing viscosity of the ingredients and promote it's packing. In some embodiments, the order of the manufacturing steps may depend on the specific equipment used and/or on the properties of the pharmaceutical agent.

According to some embodiments there is provided a matrix carrier composition for use in pharmaceutical delivery system, the composition comprising an intermolecular association of at least: a first solid phase comprising nanoparticles having hydrophobic surface, wherein the size of the nanoparticles is in the range of about 5-1000 nm; a second solid phase, comprising a biopolymer having hydrophilic and hydrophobic parts; and a continuous phase comprising oil associated with said first and said second solid phases.

According to some embodiments, the density of the first solid phase is higher than 1.4 g/cm$^3$. In some embodiments, the nanoparticles have a surface modified to be hydrophobic. The nanoparticles may be practically insoluble in water. The nanoparticles may include silica nanoparticles. The nanoparticles may include fumed silica nanoparticles. The nanoparticles may include zinc oxide nanoparticles. The nanoparticles may include carbon nanoparticles. The nanoparticles may include titanium oxide nanoparticles. In some embodiments, the nanoparticles may include a mixture of nanoparticles selected from silica, zinc oxide, titanium oxide, and carbon.

According to further embodiments, the biopolymer may be linear in structure, cyclic in structure and/or branched is structure. The biopolymer may include a saccharide. The biopolymer may include a polysaccharide. The polysaccharide may include starch, dextrin, cellulose, chitin, alpha glucan, beta glucan, amylopectin, glycogen, chitosan, cyclodextrin, mucopolysaccharide, or derivatives or combination thereof. In some embodiments, the biopolymer includes a structural protein. The structural protein may include a high molecular weight structural protein. The structural protein may include a fibrous protein. The structural protein may include a scleroprotein. The structural protein may include elastin, collagen, keratin, fibrinogen or any combination thereof.

According to further embodiments, the oil may include one or more naturally-occurring oils. The oil may include non-polar oil having polar regions. In some embodiments, the oil is selected from a group consisting of sesame oil, olive oil, linseed oil, evening primrose oil, silicone oil, and sea buckthorn oil, palm oil, or any combination thereof. In some embodiments, the oil may be selected from a group consisting of sunflower oil, corn oil, soybean oil, jojoba oil, marrow oil, grapeseed oil, hazelnut oil, apricot oil, macadamia oil, palm oil, almond oil, castor oil, and the like, or any combination thereof. In some embodiments, the oil may include lanolin. In some embodiments, the oil may include a synthetic oil. In some embodiments, the oil may include one or more naturally-occurring oils, one or more synthetic oil, or any combination thereof. In some embodiments, the oil may include a fatty alcohol. The oil may be 2-octyldodecanol. The oil may be selected from a fatty acid ester and a phenylsilicone. The oil may be selected from phenyltrimethicones, diphenyldimethicones, and poly-methylphenylsiloxanes. In some embodiments, oil is at least one wax. In some embodiments, the oil may include oblepicha oil, jojoba oil, olive oil or combinations thereof. In some embodiments, the oil may include olive oil, linseed oil, oblepicha oil, sesame oil, palm oil or combinations thereof. In some embodiments, the oil may include jojoba oil, oblepicha oil, sesame oil, olive oil or combinations thereof. In some embodiments, the oil may include wax, jojoba oil, oblepicha oil, sesame oil, olive oil or combinations thereof. In some embodiments, the oil may include linseed oil, oblepicha oil, olive oil, palm oil or combinations thereof.

According to further embodiments, the composition may further include at least one anti-oxidant. The antioxidant may include beta-carotene.

According to further embodiments, the composition may further include an amino acid selected from the group consisting of arginine, lysine, glutamic acid, aspartic acid and histidine and combinations and derivatives thereof.

According to additional embodiments, the volume ratio between the first solid phase and the second solid phase is determined according to equation 1:

$$V1 \times c1 \leq V2 \times c2 \quad \text{(equation 1);}$$

wherein

V1 is the volume of the first solid phase;
c1 is the speed of sound in the first solid phase;
V2 is the volume of the second solid phase; and
c2 is the speed of sound in the second solid phase.

According to some embodiments the composition may further include at least one active pharmaceutical agent. The composition may further include an enhancer. The composition may further include a targeting agent. The composition may further include at least one nutritional agent.

According to some embodiments, the composition may be adapted for oral administration.

According to additional embodiments, the composition may be adapted for parenteral administration.

According to some embodiments, there is provided a method for manufacturing a matrix carrier composition for use in a pharmaceutical composition, the method includes: mixing a first solid phase with an oil, wherein the first solid phase comprises nanoparticles having hydrophobic surface and particle size of about 5-1000 nm; activating a second solid phase, wherein the second solid phase comprises a biopolymer having hydrophilic and hydrophobic parts; adding the activated second solid phase into an oil; and mixing the oil comprising the first solid phase and the oil comprising the activated second solid phase.

In some embodiments, activating includes milling, vacuum treatment, chemical treatment, ultrasonic treatment or any combination thereof.

In some embodiments, one or more steps of the method may be performed under vacuum or in an inert atmosphere.

In some embodiments, the method may further include homogenization of the mixture of the oil comprising the first solid phase and the oil comprising the activated second solid phase.

In some embodiments, the method may further include maturation of the matrix carrier composition for about 1 to 72 hours. The maturation may be performed at a temperature in the range of about 1-25° C.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

Figure 1:
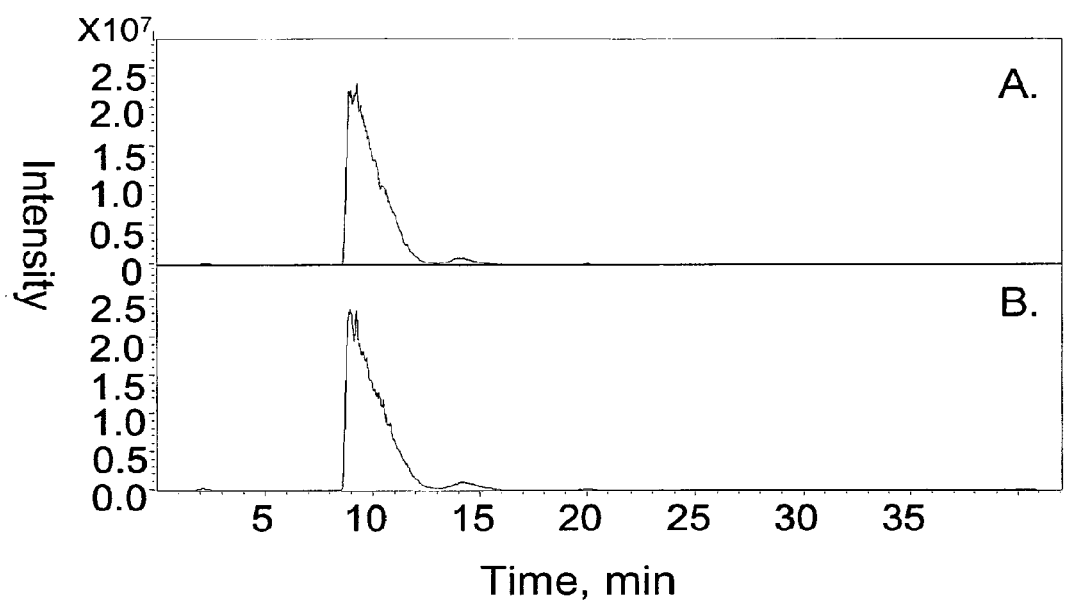
FIG. 1: LC/MS chromatograms of Insulin samples within and without a Matrix Carrier formulation, according to some embodiments.

According to some embodiments there is provided a matrix carrier composition for use in a pharmaceutical composition/pharmaceutical delivery system, with a pharmaceutical agent. The matrix comprises an intermolecular association of at least: a first solid phase, which preferably includes nanoparticles with size in range 5-1000 nm having hydrophobic surface; a second solid phase, preferably a biopolymer having both hydrophilic and hydrophobic ends; and a Continuous phase of oil associated with the components of the composition.

According to some embodiments, the second solid phase is comprised of biopolymer that may be linear, branched, cyclic or any combination thereof.

In some embodiments, the pharmaceutical agent may include a pharmaceutical drug (a substance intended for use in the medical cure, treatment, prevention and/or diagnosis of health related condition). In some embodiments, the pharmaceutical agent is a nutritional agent (a preparation intended to supplement a diet and provide nutrients, such as, for example, vitamins, minerals, fiber, fatty acids, or amino acids, that may be missing or may not be consumed in sufficient quantity in a person's diet). In some embodiments, the pharmaceutical agent is a cosmetic agent (an agent used to treat, prevent, cosmetic related conditions).

In some embodiments, the matrix carrier compositions for use in a delivery system are suitable for oral administration.

In some embodiments, the matrix carrier compositions for use in a delivery system are suitable for parenteral administration.

As used in the present specification, the following words and phrases are generally intended to have the meanings as set forth below, except to the extent that the context in which they are used indicates otherwise.

As used herein, the terms "non-covalent interaction", "non-covalent bond", and "non-covalent forces" may be used interchangeably and refer to the interaction, also referenced as association, of a first substance and a second substance wherein a covalent bond is not formed between the two substances. Non-limiting, representative interactions are van der Waals interactions, hydrogen bonding, and electrostatic interactions (also called ionic bonding).

As used herein, the terms "treating" and "treatment" with respect to a disease or condition, refer to taking steps to obtain beneficial or desired results, including but not limited to, alleviation or amelioration of one or more symptoms of the disease or condition, diminishment of extent of the disease or condition, prevention of the onset of the disease or condition, delay or slowing of progression, amelioration, palliation or stabilization of the disease or condition, partial or complete remission, prolonged survival and other beneficial results known in the art.

As used herein, the term "pharmaceutical agent" is directed to any substance, molecule, and like, which may have an effect on one or more health and/or nutritional and/or cosmetic related conditions. In some embodiments, a pharmaceutical agent may include a "pharmaceutical drug" or a combination of pharmaceutical drugs. The term "pharmaceutical drug" (interchangeably referred to herein as "drug") refers to a substance which may be intended for use in the medical cure, treatment, prevention and/or diagnosis of a health related condition (such as, for example, a disease). The term "pharmaceutical drug" is intended to include substances having pharmacological and/or pharmaceutical, and/or biological activity. In some embodiments, the pharmaceutical agent may include a nutritional agent or a combination of nutritional agents. The term "nutritional agent" refers to a substance intended to supplement a diet and provide nutrients, such as, for example, vitamins, minerals, fiber, fatty acids, or amino acids, that may be missing or may not be consumed in sufficient quantity in the diet. In some embodiments, the pharmaceutical agent may include a cosmetic agent or a combination of cosmetic agents. The term cosmetic agent refers to a substance used to treat and/or prevent, cosmetic related conditions. In some embodiments the pharmaceutical agent may include any combination of a pharmaceutical drug, a nutritional agent, and/or a cosmetic agent.

As used herein, the terms "pharmaceutical composition", "delivery system" and "pharmaceutical delivery system" may interchangeably by used. The terms refer to any applicable type of delivery system/pharmaceutical composition that may be used with the matrix carrier of the present disclosure to deliver a pharmaceutical agent (as defined herein).

As used herein, "intimate mixture" refers to a physical mixture of at least two components which are in direct physical contact with each other. For example, one component may coat the other component or one component may adhere directly to the outer surface of the particle comprising the other component. Alternately, the material of one component may be intermingled or intertwined with the other component.

As used herein, the term "potency" refers to the dose of pharmaceutical agent required to produce a specific effect of given intensity as compared to standard reference. Potency is a comparative rather than an absolute expression of the agent activity. Drug potency depends on various factors, such as one or more of bioavailability, targeting, lifetime in body fluid circulation and efficacy.

As used herein, "ADME" is an acronym in pharmacokinetics and pharmacology for Absorption, Distribution, Metabolism, and Excretion of an administered pharmaceutical drug, and describes the disposition of a pharmaceutical drug (compound) within an organism. All four ADME criteria may influence the drug levels and kinetics of drug exposure to the tissues and hence may influence the performance and pharmacological activity of the compound as a drug. Absorption may determine the compound's bioavailability whereas the drug's half life is determined by its distribution, metabolism, and removal from the body via excretion.

As used herein, the term "bioavailability" refers to the fraction of an administered dose of intact drug that reaches the systemic circulation. Bioavailability is largely determined by the properties of the dosage form, rather than by the pharmaceutical agent's physiochemical properties, which determine absorption potential. By definition, when a drug is administered intravenously (IV), its bioavailability is 100%. When a drug is orally administered, its bioavailability typically decreases.

Age, gender, physical activity, genetic phenotype, stress, disorders (such as, for example, achlorhydria and malabsorption syndromes), previous GI surgery (eg, bariatric surgery), and the like, may also affect drug bioavailability. Chemical reactions that reduce absorption can reduce bioavailability. Such reactions include, for example, formation of a complex (for example between tetracycline and polyvalent metal ions), hydrolysis by gastric acid or digestive enzymes (for example, penicillin and chloramphenicol palmitate hydrolysis), conjugation in the intestinal wall (for example, sulfoconjugation of isoproterenol), adsorption to other drugs (for example, digoxin to cholestyramine), and metabolism by luminal microflora.

As used herein, the term "half life" refers to the duration of action of a drug, i.e., the period of time required for the concentration or amount of drug in the body to be reduced by one-half. A drug molecule that leaves plasma may have one or more of several fates. For example, the drug molecule can be eliminated from the body by the kidneys or by the liver. The removal of a drug from the plasma is known as clearance, and the distribution of the drug in the various body tissues is known as the volume of distribution. Both of those pharmacokinetic parameters are related to the determination of the half life of a drug.

"Branched" as used herein encompasses both biopolymers that are naturally branched and those engineered to be branched by at least one physical treatment, such as thermal and ultrasound treatments. "Branched" is also intended to encompass biopolymers wherein a substituent of a monomer subunit of the biopolymer is replaced by another covalently bonded chain of the biopolymer. In some embodiments, the branched biopolymer is crosslinked. In some embodiments, the branched biopolymer is not crosslinked.

As used herein, the term "saccharide" refers to any simple carbohydrate including monosaccharides, monosaccharide derivatives, monosaccharide analogs, and sugars, including those which form the individual units in a polysaccharide. As used herein, the term "monosaccharide" refers to polyhydroxyaldehyde (aldose) or polyhydroxyketone (ketose)

and non-polysaccharide derivatives and analogs thereof. As used herein, the term "polysaccharide" refers to polymers formed from about 500 to over 100,000 saccharide units linked to each other by hemiacetal or glycosidic bonds. The polysaccharide may be either straight chain, singly branched, or multiply branched wherein each branch may have additional secondary branches, and the monosaccharides may be standard D- or L-cyclic sugars in the pyranose (6-membered ring) or furanose (5-membered ring) forms such as D-fructose and D-galactose, respectively, or they may be cyclic sugar derivatives, for example amino sugars such as D-glucosamine, deoxy sugars such as D-fucose or L-rhamnose, sugar phosphates such as D-ribose-5-phosphate, sugar acids such as D-galacturonic acid, or multi-derivatized sugars such as N-acetyl-D-glucosamine, N-acetylneuraminic acid (sialic acid), or N-sulfato-D-glucosamine. When isolated from nature, polysaccharide preparations comprise molecules that are heterogeneous in molecular weight. Non-limiting examples of polysaccharides include, among other compounds, galactomanans and galactomannan derivatives; galacto-rhamnogalacturons and galacto-rhamnogalacturon derivatives, and galacto-arabinogalacturon and galacto-arabinogalacturon derivatives.

As used herein, the term "beta-glucan" refers to those polysaccharides which comprise D-glucopyranosyl units which are linked together by (1→3) or (1→4) beta-linkages. Beta-Glucans occur naturally in many cereal grains such as oats and barley. The molecular weight of beta-glucan molecules occurring in cereals is, for example, from 200 to 2000 kDa.

As used herein, the term "dextrin" refers to a low-molecular-weight carbohydrate produced by the hydrolysis of starch. In some embodiments, the term refers to a linear $\alpha$-(1,4)-linked D-glucose polymer starting with an $\alpha$-(1,6) bond or a mixture of same. Dextrins are widely commercially available and can be produced inter alia by digestion of branched amylopectin or glycogen with $\alpha$-amylase. A non-limiting example of a dextrin is a maltodextrin. But there are many different types of dextrin known, and those different types can be used in other embodiments.

As used herein, the term "fibrous polymer" refers to a polymer in the form of a network of discrete thread-shaped pieces. As used herein, the terms "fiber" and "dietary fiber" refer to compounds, including but not limited to indigestible residue, plant cell polysaccharides, and lignin, all of which are resistant to hydrolysis by human digestive enzymes. Non-limiting examples of fibers are members selected from guar gum, pectin, fructo-oligosaccharides and derivatives thereof. Small amounts of other indigestible compounds, such as phytates, tannins, saponins and cutin, may be included in dietary fiber since these compounds are indigestible and associated with dietary fiber polysaccharides.

As used herein, "silica" refers to silicon dioxide. Silica is widely recognized as a safe food additive (Thirteenth report of the Joint FAO/WHO Expert Committee on Food Additives, FAO Nutrition Meetings Report Series; from the Joint FAO/WHO Expert Committee on Food Additives meeting in Rome, May 27-Jun. 4, 1969).

As used herein, the term "silicate" refers to a compound containing silicon and oxygen, e.g. in tetrahedral units of $SiO4$. In other embodiments, the term refers to a compound containing an anion in which at least one central silicon atom is surrounded by electronegative ligands. Non-limiting, representative examples of silicates are hexafluorosilicate, sodium silicate ($Na2SiO3$), aluminum silicates, and magnesium silicates.

As used herein, the term "wax" means a lipophilic compound, which is solid at room temperature (25° C.), with a reversible solid/liquid change of state, having a melting point of greater than or equal to 30° C., which may be up to 120° C.

In some embodiments, the present invention provides a matrix carrier composition, which includes pharmacologically inert nanoparticles, in non-covalent association with a biopolymer and a lipid comprising non-polar and polar bonds, with pharmaceutical agent, wherein the inert nanoparticles include silica nanoparticles, and wherein the diameter of the nanoparticles is between 1-1000 nanometers, and wherein the biopolymer includes a combination of branched and non-branched biopolymers, and wherein the lipid includes a mix of the synthetic and/or natural saturated and unsaturated fatty acids which associated with nanoparticles, biopolymer or carbohydrate and including pharmaceutical agent and in some embodiments enhancer and or targeting agent. Each possibility represents a separate embodiment of the present invention.

In some embodiments, the present invention provides a matrix carrier composition, comprising pharmacologically inert nanoparticles, in non-covalent association with a biopolymer, wherein the inert nanoparticles includes silica nanoparticles, and wherein the diameter of the nanoparticles is between 1-1000 nanometers, and the nanoparticle-biopolymer complex is associated with the oil, and wherein the particle diameter of the matrix carrier composition is between 100-500,000 nanometers (nm). In certain preferred embodiments, the particle diameter of the matrix carrier composition is between 100-50,000 nm. In another embodiment, the oil phase of the matrix carrier composition comprises a plurality of oils. Each possibility represents a separate embodiment of the present invention.

In another embodiment, the matrix carrier composition is held together by non-covalent forces. In another embodiment, without wishing to be bound by any theory or mechanism of action, the non-covalent forces between the components of the matrix composition enable the matrix composition to self-assemble when the components are mixed together, as described herein. In another embodiment, without wishing to be bound by any theory or mechanism of action, the matrix carrier includes two solid phases containing at least two solid pharmacologically inert materials (nanoparticles and biopolymers) with different properties. In another embodiment, the non-covalent forces cause the nanoparticles and biopolymer to form a mixture. In another embodiment, the matrix composition exhibits an ordered, fractal structure. Each possibility represents a separate embodiment of the present invention. The structure and composition of the matrix carrier may allow the use of the matrix carrier in various administration routes, such as, for example by oral administration, by parenteral routes, topical, and the like.

In another embodiment, without wishing to be bound by any theory or mechanism of action, the energy of non-covalent bonds between a pharmaceutical agent and the matrix carrier may be less than about 10 kcal per mole (such as in the range of about 1 to 5 kcal per mole). This value is higher than the energy of thermal fluctuations at 37° C. (about 0.615 kcal per mole), which is enough for keeping or protection the pharmaceutical agent in gastro-intestinal tract. This energy is relatively close, for example, to the bond energy between insulin and its receptor. This may provide a possible control of pharmacokinetics and pharmacodynamics of the pharmaceutical agent. In some embodiments, the matrix carrier may provide protection from biodegradation of the pharmaceutical agent at 37° C. in the stomach (acid solution of pepsin and other enzymes) and small intestine (neutral solution of the pancreatic enzymes, bile acids salts, etc) for more than 8 hours.

In some embodiments, the matrix carrier may release the pharmaceutical agents due to action of synthetic surfactants (such as, for example, TWEEN 20, TWEEN 80, and the like) or natural surfactants of body fluids (such as, for example, blood, lymph, interstitial fluid, and the like).

In another embodiment, the nanoparticle-biopolymer complex is dispersed within the oil phase of the matrix composition. In another embodiment, the oil phase is impregnated with the nanoparticle-biopolymer complex of the matrix composition. As provided herein, the present invention provides compositions wherein the nanoparticles and biopolymer form a matrix that is impregnated and completely surrounded by the oil phase. Each possibility represents a separate embodiment of the present invention.

Oil having particulate matter associated therewith refers to particulate matter that is in contact with oil. For example "associated with" may include embedded, dispersed, immersed, suspended, and the like, within the oil. The composition as a whole need not be homogeneous with regard to the distribution of the particulate matter. Rather, the particulate matter is capable of being embedded, dispersed, immersed, suspended, and the like, in the oil when agitated. The particulate matter need not be completely homogeneous, but rather is characterized by its containing the ingredients specified herein and its contact with the oil of the present invention. Compositions wherein the particulate matter is agglomerated fall within the scope of the present invention The Matrix Carrier Composition According to some embodiments, there is provided a matrix carrier composition for use in a pharmaceutical composition for administration, comprising an intermolecular association of at least one biopolymer, nanoparticles, and at least one oil. Administration may include various administration routes, such as, for example, but not limited to: oral administration, parenteral administration, topical administration, and the like.

That intermolecular association may take place spontaneously and result in the formation of stable structures. The course of that association process, and properties of the resulting product, may depend upon the nature of the components and/or upon the conditions under which the association takes place.

According to some embodiments, the volume ratio between the first solid phase and the volume of the second solid phase may be at a desired ratio so as to optimize the protecting properties of the matrix carrier.

The ratio of the volume of the first solid phase and the volume of the second solid phase may be determined according to the speed of sound (c) of each solid phase as following:

Speed of sound (c) in the material is a function of its density:

$$c = \sqrt{C/\rho};$$

Wherein c—is Speed of sound; C—coefficient of stiffness; ρ—density

The Second and First Solid phase volume ratio may thus be calculated according to the following equation (equation 1):

$$V1 \times c1 \leq V2 \times c2 \quad \text{(Equation 1);}$$

wherein V1—volume of the First Solid Phase; c1—Speed of Sound in the First Solid Phase; V2—volume of the Second Solid Phase; c2—Speed of Sound in the Second Solid Phase.

In some embodiments, that intermolecular association comprises a network of non-covalent interactions between the at least one biopolymer, the nanoparticles, and the at least one oil. That is, the recited components may be held together by non-covalent forces. In some embodiments, without wishing to be bound by any theory or mechanism of action, the non-covalent forces enable the components to self-assemble when the components are blended together. In some embodiments, again without wishing to be bound by any theory or mechanism of action, the non-covalent forces cause the nanoparticles and biopolymer to form an intimate mixture. In some embodiments, again without wishing to be bound by any theory or mechanism of action, the association results in an ordered, fractal structure.

In some embodiments, without wishing to be bound by any theory or mechanism of action, matrix carrier compositions described herein may be converted in the digestive system to particles smaller in size but similar in structure to the original composition, which are absorbed similarly to fat drops and like chylomicrons reach the bloodstream with or without undergoing first-pass metabolism in the liver.

In some embodiments, without wishing to be bound by any theory or mechanism of action, the energy of non-covalent bonds between a pharmaceutical agent and the matrix carrier may be less than about 10 kcal per mole (such as in the range of about 1 to 5 kcal per mole). This value is higher than the energy of thermal fluctuations at 37° C. (about 0.615 kcal per mole), which is enough for keeping or protection the pharmaceutical agent in gastro-intestinal tract. This energy is relatively close, for example, to the bond energy between insulin and its receptor. This may provide a possible control of pharmacokinetics and pharmacodynamics of the pharmaceutical agent. In some embodiments, the matrix carrier may provide protection from biodegradation of the pharmaceutical agent at 37° C. in the stomach (acid solution of pepsin and other enzymes) and small intestine (neutral solution of the pancreatic enzymes, bile acids salts, and the like) for more than 2 hours. In some embodiments matrix carrier provides protection for more than 4 hours, more than 6 hours, more than 8 hours, more than 12 hours, more than 16 hours. In some embodiments, the matrix carrier may release and preserve the activity of the pharmaceutical agent after treatment by surfactants which, may cause disassembly of the matrix complex, associated by non-covalent bonds (as further demonstrated in Example 7).

According to some embodiments, without wishing to be bound by any theory or mechanism of action, the matrix carrier compositions described herein may provide protection of the pharmaceutical agent from the external environment. In some embodiments, the matrix carrier compositions described herein may enable oral delivery of the pharmaceutical agent. In some embodiments, the matrix carrier compositions described herein may modulate the pharmacokinetics and/or pharmacodynamics of pharmaceutical agents administered by oral and/or parenteral route, as compared to other administration routes and/or use of other pharmaceutical compositions and formulations.

In some embodiments, the intermolecular association comprises a network of non-covalent interactions between the at least one biopolymer, the nanoparticles, and the at least one oil, wherein there is additionally one or more covalent bonds between the at least one biopolymer and the nanoparticles, and/or between the at least one biopolymer and the at least one oil, and/or between the at least one at least one oil and the nanoparticles. For example, in some embodiments, at least a portion of the at least some of the nanoparticles, and more particularly, silica nanoparticles, is covalently bonded to the biopolymer, according to methods known by those skilled in the art.

In some embodiments, the biopolymer and/or the nanoparticles are dispersed within the at least one oil. In some embodiments, the biopolymer and/or the nanoparticles are suspended in the at least one oil. In some embodiments, the biopolymer and/or the nanoparticles are embedded within the at least one oil. In some embodiments, the at least one oil is impregnated with the biopolymer and/or the nanoparticles. In some embodiments, the associated nanoparticles and biopolymer form a matrix that is impregnated and surrounded by the at least one oil. In some embodiments, the nanoparticles and biopolymer are otherwise associated with the at least one oil.

In some embodiments there is provided a matrix carrier pharmaceutical composition with a pharmaceutical agent, the matrix comprises an intermolecular association of at least:
1. First solid phase, preferably nanoparticles with size in range 5-1000 nm having hydrophobic surface;
2. Second solid phase, preferably biopolymer having both hydrophilic and hydrophobic parts; and
3. Continuous phase of oil associated with the components of the matrix carrier pharmaceutical composition.

According to some embodiments, the matrix carrier composition need not be homogeneous, but rather may be characterized by its containing the ingredients specified herein.

According to some embodiments, the matrix carrier composition is suspension. In some embodiments, the matrix carrier composition is emulsion. In some embodiments, the matrix carrier forms in water environment a water based emulsion wherein non-polar phase is suspension.

In some embodiments, the matrix carrier composition is agglomerated.

In some embodiments the weight of the at least one biopolymer may be at least equal to that of the nanoparticles. In some embodiments, the weight of the at least one biopolymer may be greater than the weight of the nanoparticles. In some embodiments the weight of the at least one biopolymer may be at least twice that of the nanoparticles. In some embodiments the weight of the at least one biopolymer may be fivefold that of the nanoparticles. In some embodiments the weight of the at least one biopolymer may be at least ten times greater than the weight of nanoparticles. In some embodiments the at least one biopolymer may be at least one hundred times greater than the weight of nanoparticles.

In some embodiments, the matrix carrier comprises an intermolecular association of at least one biopolymer, silica nanoparticles, and at least one oil.

In some embodiments, the matrix carrier comprises an intermolecular association of at least one biopolymer comprising a polysaccharide, nanoparticles, and at least one oil.

In some embodiments, the matrix carrier comprises an intermolecular association of at least one biopolymer comprising a branched polysaccharide, silica nanoparticles, and at least one oil.

In some embodiments, the matrix carrier comprises an intermolecular association of at least one biopolymer comprising a branched polysaccharide, nanoparticles, and at least one oil.

In some embodiments, the matrix carrier composition is not composed of silica nanoparticles having a hydrophobic surface, a polysaccharide, and at least one oil.

In some embodiments, when the matrix carrier composition is to be used for the oral administration of insulin, the matrix carrier composition is not composed of olive oil, a dietary fiber, silica nanoparticles, oblepicha oil, and sesame oil. In some embodiments, when the matrix carrier composition is to be used for the oral administration of insulin, the matrix carrier composition is not composed of olive oil, rice polysaccharides, silica nanoparticles, oblepicha oil, and evening primrose oil. In some embodiments, when the matrix carrier composition is to be used for the oral administration of insulin, the matrix carrier composition is not composed of olive oil, a dietary fiber, silica nanoparticles, oblepicha oil, evening primrose oil, and linseed oil. In some embodiments, when the matrix carrier composition is to be used for the oral administration of insulin, the matrix carrier composition is not composed of olive oil, a dietary fiber, oblepicha oil, silica nanoparticles, and sesame oil. In some embodiments, when the matrix carrier composition is to be used for the oral administration of insulin, the matrix carrier composition is not composed of olive oil, oblepicha oil, sesame oil, amylopectin, chitin, and silica nanoparticles. In some embodiments, when the matrix carrier composition is to be used for the oral administration of insulin, the matrix carrier composition is not composed of olive oil, rice polysaccharides, silica nanoparticles, oblepicha oil, and sesame oil. In some embodiments, when the matrix carrier composition is to be used for the oral administration of insulin, the matrix carrier composition is not composed of olive oil, a dietary fiber, oblepicha oil, silica nanoparticles, and sesame oil. In some embodiments, when the matrix carrier composition is to be used for the oral administration of insulin, the matrix carrier composition is not composed of olive oil, rice polysaccharides, silica nanoparticles, oblepicha oil, and evening primrose oil. In some embodiments, when the matrix carrier composition is to be used for the oral administration of insulin, the matrix carrier composition is not composed of olive oil, oblepicha oil, sesame oil, amylopectin, chitin, and silica nanoparticles.

In some embodiments, when the matrix carrier composition is to be used for the oral administration of erythropoietin, the matrix carrier composition is not composed of olive oil, rice polysaccharides, silica nanoparticles, oblepicha oil, and linseed oil.

In some embodiments, when the matrix carrier composition is to be used for the oral administration of growth hormone, the matrix carrier composition is not composed of amylopectin from maize, silica nanoparticles, olive oil, oblepicha oil, and sesame oil.

In some embodiments, when the matrix carrier composition is to be used for the oral administration of copaxone, the matrix carrier composition is not composed of jojoba oil, olive oil, alpha-glucan, beta-glucan, amylopectin, silica nanoparticles, oblepicha oil, and sesame oil.

In some embodiments, when the matrix carrier composition is to be used for the oral administration of copaxone, the matrix carrier composition is not composed of oblepicha oil, olive oil, beta-glucan, amylopectin, silica nanoparticles, and beeswax.

In some embodiments, when the matrix carrier composition is to be used for the oral administration of Apolipoprotein A-mimetic peptide, the matrix carrier composition is not composed of oblepicha oil, olive oil, beta-glucan, chitin, amylopectin, silica nanoparticles, and beeswax.

In some embodiments, when the matrix carrier composition is to be used for the oral administration of Rituxan, the matrix carrier composition is not composed of oblepicha oil, olive oil, chitin, amylopectin, silica nanoparticles, and beeswax.

In some embodiments, when the matrix carrier composition is to be used for the oral administration of DNase, the matrix carrier composition is not composed of jojoba oil, oblepicha oil, rice polysaccharides, silica nanoparticles, olive oil, and sesame oil. In some embodiments, when the matrix carrier composition is to be used for the oral administration of DNase, the matrix carrier composition is not composed of jojoba oil, oblepicha oil, a dietary fiber, silica nanoparticles, olive oil, and sesame oil.

In some embodiments, when the matrix carrier composition is to be used for the oral administration of RNase, the matrix carrier composition is not composed of rice polysaccharides, silica nanoparticles, linseed oil, oblepicha oil, olive oil, sesame oil, L-glutamic acid, glycine, L-lysine, and L-arginine.

In some embodiments, when the pharmaceutical agent is a protein or peptide having therapeutic activity, the pharmaceutical composition is not composed of silica nanoparticles having a hydrophobic surface, a polysaccharide, and at least one oil.

In some embodiments, the pharmaceutical agent is not a protein or peptide having therapeutic activity.

First Solid Phase—Nanoparticles

The nanoparticles generally will have a surface capable of forming an intermolecular association with the at least one biopolymer with the oil. In some embodiments, the nanoparticles have a hydrophobic surface. Reference to a "hydrophobic" surface indicates, in some embodiments, that at least 40% of the nanoparticle surface is hydrophobic (for example, at least 50%, 50-60%, 60-70%, or 70-100%), with the remainder of the surface being non-hydrophobic.

In some embodiments, the nanoparticles have a surface modified to be hydrophobic, and in some of those embodiments at least 40% of the nanoparticle surface is hydrophobic (for example, at least 50%, 50-60%, 60-70%, or 70-100%), with the remainder of the surface being non-hydrophobic. In some embodiments, the nanoparticles are modified by coating the surface with a hydrocarbon. In some embodiments, the coating causes the nanoparticles to display hydrocarbon moieties on their surface. In some embodiments, the hydrocarbon moieties are selected from methyl, ethyl, propyl, isopropyl, butyl, isobutyl, T-butyl, pentyl, and iso-pentyl. In some embodiments, the coating causes the nanoparticles to display methyl moieties on their surface.

In some embodiments, the nanoparticles are silica nanoparticles, which use is known in the art, as disclosed, for example, in U.S. Pat. Nos. 6,322,765 and 6,698,247.

In some embodiments the inert nanoparticles include silica nanoparticles, where at least 80% of silica is hydrophobic silica. In some embodiments the inert nanoparticles include silica nanoparticles, where at least 90% of silica is hydrophobic silica. In some embodiments the inert nanoparticles include silica nanoparticles, where at least 95% of silica is hydrophobic silica.

In some embodiments, the density of the first solid phase may be higher than 1.2 g/cm$^3$. In some embodiments, the density of the first solid phase may be higher than 1.3 g/cm$^3$. In some embodiments, the density of the first solid phase may be higher than 1.4 g/cm$^3$. In some embodiments, the density of the first solid phase may be higher than 1.5 g/cm$^3$.

Methods for imparting a hydrophobic surface to nanoparticles are well-known in the art, and are also described herein. In some embodiments, the surface of the nanoparticle, e.g., when the nanoparticle comprises fumed silica, may be chemically modified to decrease the number of silanol groups. For example, silanol groups can be substituted with hydrophobic groups to obtain a hydrophobic silica. The hydrophobic groups can be:

trimethylsiloxy groups, which are obtained, for example, by treatment of fumed silica in the presence of hexamethyldisilazane. Silicas thus treated are known as "silica silylate" according to the CTFA (6th edition, 1995). They are sold, for example, under the references "Aerosil R812®" by the company Degussa and "CAB-OSIL TS-530®" by the company Cabot; dimethylsilyloxy or polydimethylsiloxane groups, which are obtained, for example, by treatment of fumed silica in the presence of polydimethylsiloxane or dimethyldichlorosilane. Silicas thus treated are known as "silica dimethyl silylate" according to the CTFA (6th edition, 1995). They are sold, for example, under the references "Aerosil R972®.", "Aerosil R974®" by the company Degussa, "CAB-O-SIL TS-610®." and "CAB-O-SIL TS-720®", by the company Cabot.

Other methods for imparting a hydrophobic surface to nanoparticles are well-known in the art and are described in various documents, such as, for example: Chung et al (Hydrophobic modification of silica nanoparticle by using aerosol spray reactor. Colloids and Surfaces A: Physicochem. Eng. Aspects 236 (2004) 73-79); Fu X, et. al. (Physicochem. Eng. Aspects 179: 65, 2001); Krysztafkiewicz A, et. al. (Colloids Surf. A: Physicochem. Eng. Aspects 173:73, 2000); Jean J and Yang S, J (Am. Ceram. Soc. 83(8):1928, 2000); Zhang J and Gao L. (Ceram. Int. 27: 143, 2001); US Patent applications: US 2007/0172426, US 2006/0053971, US 2007/0098990.

In some embodiments, the nanoparticles are practically insoluble in water. "Practically insoluble" refers, in some embodiments, to a substance having a solubility of less than 100 parts per million weight/weight (ppm). In some embodiments, the term refers to a solubility of less than 200 ppm. In some embodiments, the term refers to a solubility of less than 80 ppm. In some embodiments, the term refers to a solubility of less than 60 ppm. In some embodiments, the term refers to a solubility of less than 50 ppm. In some embodiments, the term refers to a solubility of less than 40 ppm. In some embodiments, the term refers to a solubility of less than 30 ppm. In some embodiments, the term refers to a solubility of less than 20 ppm. In some embodiments, the term refers to a solubility of less than 15 ppm. In some embodiments, the term refers to a solubility of less than 10 ppm.

In some embodiments, the nanoparticles are pharmacologically inert. In some embodiments, the nanoparticles are composed of materials that are generally recognized as safe (GRAS). In some embodiments, the nanoparticles are non-toxic. In some embodiments, the nanoparticles are non-teratogenic. In some embodiments, the nanoparticles are biologically inert.

In some embodiments, the nanoparticles comprise silica nanoparticles. In some embodiments, the nanoparticles comprise fumed silica nanoparticles.

"Silica nanoparticles" refers, for example, to nanoparticles selected from silica, silicates, and combinations thereof.

Silica nanoparticles are available commercially, e.g. as 99.99% pure finely ground silica. It will be understood by those skilled in the art that lower grades of purity of silica may be used.

In some embodiments, the nanoparticles are a single type. In some embodiments, the nanoparticles are of multiple types. In some embodiments, the nanoparticles are a mixture of silica nanoparticles and other types of nanoparticles. In some embodiments, essentially all the nanoparticles are silica nanoparticles.

In some embodiments, the nanoparticles comprise zinc oxide nanoparticles.

In some embodiments, the nanoparticles comprise carbon nanoparticles.

In some embodiments, the nanoparticles comprise titanium oxide nanoparticles.

In some embodiments, the nanoparticles comprise nanoparticles other than silica nanoparticles but having a hardness similar to that of silica nanoparticles.

In some embodiments, the nanoparticles comprise a mixture of nanoparticles selected from silica, zinc oxide, titanium oxide, and carbon.

In some embodiments, the nanoparticles comprise silver nanoparticles and/or compound silver nanoparticles.

In some embodiments, the nanoparticles comprise gold nanoparticles and/or compound gold nanoparticles.

In some embodiments, the nanoparticles comprise platinum nanoparticles and/or compound platinum nanoparticles.

In some embodiments, the nanoparticles comprise a mixture of nanoparticles selected from gold, platinum and silver and any combination or compounds thereof.

In some embodiments, the mean diameter of the nanoparticles is from 1 to 800 nanometers (nm). In some embodiments, the mean diameter is from 2 to 400 nm. In some embodiments, the mean diameter is from 2 to 300 nm. In some embodiments, the mean diameter is from 3 to 200 nm. In some embodiments, the mean diameter is from 4 to 150 nm. In some embodiments, the mean diameter is from 4 to 100 nm. In some embodiments, the mean diameter is from 1 to 100 nm. In some embodiments, the mean diameter is from 5 to 50 nm. In some embodiments, the mean diameter is from 5 to 40 nm. In some embodiments, the mean diameter is from 5 to 30 nm. In some embodiments, the mean diameter is from 7 to 40 nm. In some embodiments, the mean diameter is from 6 to 25 nm. In some embodiments, the mean diameter is from 10 to 11 nm. In some preferred embodiments, the mean diameter of the nanoparticles is from 5 to 600.

In some embodiments, the average diameter is about 5 nm. In some embodiments, the average diameter is about 6 nm. In some embodiments, the average diameter is about 7 nm. In some embodiments, the average diameter is about 8 nm. In some embodiments, the average diameter is about 9 nm. In some embodiments, the average diameter is about 10 nm. In some embodiments, the average diameter is about 12 nm. In some embodiments, the average diameter is about 14 nm. In some embodiments, the average diameter is about 16 nm. In some embodiments, the average diameter is about 18 nm. In some embodiments, the average diameter is about 20 nm. In some embodiments, the average diameter is another diameter falling within a range disclosed herein.

In some embodiments, the nanoparticles have a melting temperature falling within a range suitable for the matrix carrier compositions described herein. In some embodiments, the nanoparticles have a melting temperature (Tm) of over 600° C. In some embodiments, the Tm is from 600 to 4500° C., e.g., in some embodiments, the Tm is from 800 to 4500° C. In some embodiments, the Tm is any Tm falling within a range disclosed herein. Tm may be determined using techniques well known for defining melting temperatures for metals or nanoparticles.

Second Solid Phase—Biopolymer(s)

According to some embodiments the second phase of the matrix carrier, may include one or more biopolymers.

According to some embodiments, the biopolymers used in methods and compositions of the present invention may include any biopolymer known in the art. For example, the biopolymer may include a linear polymer, a branched polymer, an unbranched polymer, a cyclic biopolymer, and the like. The Biopolymer may be naturally-occurring, hemi-synthetic, or synthetic biopolymer. In some embodiments, the biopolymer may include a monomer, a dimmer, an oligomer and/or a polymer. In some exemplary embodiments, the biopolymer includes a saccharide (a carbohydrate). In some exemplary embodiments, the biopolymer includes a polysaccharide.

In some embodiments, the "Second solid phase" comprises both hydrophilic and hydrophobic residues/parts/regions. In some embodiments, the hydrophilic and hydrophobic residues interact with the hydrophobic and/or hydrophilic regions, respectively, of the pharmaceutical agent and/or components of the "Second solid phase" and/or the nanoparticle (of the "First solid phase").

In some embodiments, one biopolymer is used. In other embodiments, more than one biopolymer is used. In some embodiments, the biopolymer is linear in structure. In some embodiments, the biopolymer is cyclic in structure. In some embodiments, the biopolymer is branched in structure.

In some embodiments, the "Second solid phase" has a melting temperature (Tm) under 400° C. In some embodiments, the Tm is below 350° C. In some embodiments, the Tm is below 300° C. In some embodiments, the Tm is below 250° C. In some embodiments, the Tm is below 200° C. In some embodiments, the Tm is below 150° C. In some embodiments, the Tm is from 100 to 400° C. In some embodiments, the Tm is any Tm falling within a range disclosed herein. Tm may be determined using standard techniques known in the art for analyzing the melting temperatures of polymers.

In some embodiments, the biopolymer is a saccharide. The saccharide is, in some embodiments, a naturally-occurring saccharide. In some embodiments, the saccharide is a synthetic saccharide.

In some embodiments, the biopolymer comprises a polysaccharide. Biopolymers such as polysaccharides have been known in the art as excipients in oral dosage forms, as disclosed, for example in U.S. Pat. No. 6,667,060 and US patent application 2004/0115264. The polysaccharide comprises, in some embodiments, a naturally-occurring polysaccharide. In some embodiments, the polysaccharide comprises a synthetic polysaccharide. Non limiting examples of synthetic polysaccharides can be found in U.S. Pat. No. 6,528,497 and in Okada M. et al. Polymer journal, 15 (11); 821-26 (1983). In some embodiments, the polysaccharide can be hemi-synthetic. In some embodiments, the biopolymer comprises at least one positively charged polysaccharide. But, whether the polysaccharide is naturally-occurring, hemi-synthetic, or synthetic, it is a biopolymer as that term is used herein.

In some embodiments, the polysaccharide comprises a branched polysaccharide. This term is well understood to those skilled in the art and can refer to any number and structure of branches in the polysaccharide. In some embodiments, the polysaccharide comprises a naturally-occurring branched polysaccharide. In some embodiments, the polysaccharide comprises a synthetic branched polysaccharide.

In some embodiments, the biopolymer of the Second solid phase may include an unbranched biopolymer. "Unbranched biopolymer" refers to linear or cyclic biopolymers. Non limiting examples of unbranched biopolymers include, for example, but not limited to glucosaminoglycans (GAGs) or mucopolysaccharides, which are long unbranched polysaccharides consisting of a repeating disaccharide unit, cyclodextrin, and the like.

In some embodiments, the biopolymer of the Second solid phase may include a carbohydrate selected from nutriose, maltsorb, xylitol, mannitol, rice polysaccharide, starch, dextrin, cellulose, chitin, alpha glucan, beta glucan, amylopectin, glycogen, chitosan, glucosaminoglycans (GAGs), mucopolysaccharides and derivatives thereof.

In some embodiments, the biopolymer of the Second solid phase may include polysaccharide comprising starch. Non-limiting examples of starch are corn starch, potato starch, rice starch, wheat starch, purum starch, and starch from algae. In some embodiments, the starch is any other starch known in the art.

In some embodiments, the biopolymer of the Second solid phase may include a polysaccharide comprising a dextrin. "Dextrin" in another embodiment refers to a low-molecular-weight carbohydrate produced by the hydrolysis of starch. In another embodiment, the term refers to a linear α-(1,4)-linked D-glucose polymer starting with an α-(1,6) bond or a mixture of same. Dextrins are widely commercially available and can be produced inter alia by digestion of branched amylopectin or glycogen with α-amylase. A non-limiting example of a dextrin is a maltodextrin having the structure below. In another embodiment, the dextrin is any other dextrin known in the art. Each possibility represents a separate embodiment of the present invention.

In some embodiments, the biopolymer of the Second solid phase may include a polysaccharide comprising cellulose. A non-limiting example of cellulose is α-cellulose. In other embodiments, the cellulose is any other cellulose known in the art.

In some embodiments, the biopolymer of the Second solid phase may include a polysaccharide comprising chitin. A non-limiting example of chitin has the molecular formula $(C_8H_{13}NO_5)n$. In other embodiments, the chitin is any other chitin known in the art.

In some embodiments, the biopolymer of the Second solid phase may include a polysaccharide comprising an alpha-glucan. Alpha-glucans may be linear or branched polymers of glucose with alpha 1-2, alpha 1-3, alpha 1-4, and/or alpha 1-6 glycosidic linkages. For example, alpha-glucans such as alpha-amylose derived from plants are unbranched linear glucose polymers with alpha 1-4 glycosidic linkages and alpha-glucans, such as amylopectin, are derived from plants and are branched glucose polymers with alpha 1-4 glycosidic linkages in the backbone and alpha 1-6 linkages at branch points. In other embodiments, the alpha-glucan is any other alpha-glucan known in the art.

In some embodiments, the biopolymer of the Second solid phase may include polysaccharide that is a beta-glucan. "Beta-glucan" refers to those polysaccharides which comprise D-glucopyranosyl units which are linked together by (1→3) or (1→4) beta-linkages. Beta-Glucans occur naturally in many cereal grains such as oats and barley and in fungus (mushrooms) and were suggested, in clinical and animal studies to increase certain aspects of the immune system. In addition, studies suggest that mushroom polysaccharides may also be able to increase dendritic cell function. The molecular weight of beta-glucan molecules occurring in cereals is typically 200 to 2000 kDa. Non limiting example of beta glucan is Lentinan, which is isolated from the shiitake mushroom. In another embodiment, the beta-glucan is any other beta-glucan known in the art. Each possibility represents a separate embodiment of the present invention. Additional examples of the beta-glucan is 346210 β-Glucan, isolated from *Saccharomyces cerevisiae* (Calbiochem production, 9008-22-4 Ref. in Merck chemicals catalogue).

In some embodiments, the biopolymer of the Second solid phase may include a polysaccharide that is a glycosamingly-can (GAG) or mucopolysaccharide, which are long unbranched polysaccharides consisting of a repeating disaccharide unit. The repeating unit may include a hexose (six-carbon sugar) or a hexuronic acid, linked to a hexosamine (six-carbon sugar containing nitrogen). Some GAG chains may be covalently linked to a protein to form proteoglycans; the exception is the GAG hyaluronan, which is uniquely synthesized without a protein core and is "spun out" by enzymes at the cell surface directly into the extracellular space. Some examples of glycosaminoglycan uses in nature include heparin as an anticoagulant, hyaluronan as a component in the synovial fluid lubricant in body joints, and chondroitins which can be found in connective tissues, cartilage and tendons. Members of the glycosaminoglycan family vary in the type of hexosamine, hexose or hexuronic acid unit they contain (e.g. glucuronic acid, iduronic acid, galactose, galactosamine, glucosamine. They may also vary in the geometry of the glycosidic linkage. Exemplary GAG include such GAGs as, but not limited to: 385908 Hyaluronic Acid, Sodium Salt, *Streptococcus* sp., Natural high-viscosity mucopolysaccharide with alternating β1,3-glucuronidic and β1,4-glucosaminidic bonds. Principal glycosaminoglycan in connective tissue fluids, Lyophized powder, (CAS 9067-32-7, Calbiochem), Mushroom polysaccharides (pharma grade), such as, for example moss, *cordyceps*, and the like.

In some embodiments, the at least one nanoparticle ("First Solid Phase") and the at least one biopolymer ("Second solid phase"), that are intermolecular associated, are particulate matter.

In some embodiments, the "Second solid phase" may include a biopolymer comprising a fibrous biopolymer, for example, a dietary fiber. Biopolymers can be either naturally fibrous or made fibrous by physical and chemical treatment. In some embodiments, the dietary fiber comprises a water insoluble fiber. In some embodiments, the dietary fiber comprises a linear insoluble fiber. In some embodiments, the dietary fiber comprises a water soluble fiber. In some embodiments, the dietary fiber comprises a linear soluble fiber.

In some embodiments, the "Second solid phase" may include a biopolymer comprising a mucopolysaccharide (such as, for example, certificated medical mushroom mucopolysaccharides by Aloha Medicinals Inc).

In some embodiments, the "Second solid phase" may include a biopolymer comprising a structural protein.

In some embodiments, the "Second solid phase" may include a biopolymer that can comprise either one or a plurality of types of biopolymers. In some embodiments, the biopolymer comprises two or more types of biopolymers. In some embodiments, the biopolymer comprises three or more types of biopolymers. In some embodiments, the biopolymer comprises four or more types of biopolymers. In some embodiments, the biopolymer comprises more than four types of biopolymers.

In some embodiments, the "Second solid phase" may include a biopolymer comprising a branched biopolymer and/or a linear biopolymer and/or cyclic biopolymer. In some embodiments, the "Second solid phase" includes a biopolymer that comprises a branched carbohydrate and a linear carbohydrate and or cyclic carbohydrate. In some embodiments, the "Second solid phase" includes biopolymer that comprise a branched carbohydrate and a linear carbohydrate and/or cyclic carbohydrate and/or any combination thereof. Each possibility represents a separate embodiment of the present invention.

In some embodiments, the "Second solid phase" may include a biopolymer comprising a branched biopolymer and a cyclic biopolymer. In some embodiments, the biopolymer comprises a branched polysaccharide and a cyclic polysaccharide. In some embodiments, the cyclic polysaccharide comprises a cyclodextrin. In some embodiments, the cyclodextrin is selected from α-cyclodextrin, β-cyclodextrin, γ-cyclodextrin and derivatives thereof. A non-limiting example of such a combination is starch based polysaccharide such as, but not limited to: amylopectin, and/or nutriose and/or cyclodextrin, such as, for example, beta-Cyclodextrin.

In some embodiments, the "Second solid phase" biopolymer comprises a branched biopolymer and a high molecular weight structural protein. In some embodiments, the biopolymer comprises a branched polysaccharide and a high molecular weight structural protein.

In some embodiments, the "Second solid phase" biopolymer comprises a linear biopolymer and a cyclic biopolymer. In some embodiments, the biopolymer comprises a linear polysaccharide and a cyclic polysaccharide. In some embodiments, the linear polysaccharide is selected from fiber, chitin, glucans and cellulose.

In some embodiments, the "Second solid phase" biopolymer comprises a branched biopolymer, a cyclic biopolymer, and a linear biopolymer. In some embodiments, the "Second solid phase" biopolymer comprises a branched polysaccharide, a cyclic polysaccharide, and a linear polysaccharide. In some embodiments, the cyclic polysaccharide comprises a cyclodextrin. In some embodiments, the linear polysaccharide is selected from chitin, glucans, fiber, maltsorb and cellulose.

In some embodiments, the "Second solid phase" biopolymer comprises a branched biopolymer, a cyclic biopolymer, and a structural protein. In some embodiments, the "Second solid phase" biopolymer comprises a branched polysaccharide, a cyclic polysaccharide, and a structural protein. In some embodiments, the branched polysaccharide comprises amylopectin. In some embodiments, the cyclic polysaccharide is a cyclodextrin, e.g., α-Cyclodextrin. In some embodiments, the structural protein is selected from melanin and keratin, wherein in some embodiments, the keratin is in a neutral-basic (keratin 1-8) or in acidic (keratin 9-20) forms.

In some embodiments, the "Second solid phase" biopolymer comprises a branched biopolymer, a structural protein, and an insoluble fiber. In some embodiments, the "Second solid phase" biopolymer comprises a branched polysaccharide, a structural protein, and an insoluble fiber. In some embodiments, the branched polysaccharide is amylopectin. In some embodiments, the structural protein is keratin.

In some embodiments, the "Second solid phase" biopolymer comprises a branched biopolymer, a linear biopolymer, and an insoluble fiber. In some embodiments, the "Second solid phase" biopolymer comprises a branched polysaccharide, a linear polysaccharide, and an insoluble fiber. In some embodiments, the branched polysaccharide is amylopectin. In some embodiments, the linear polysaccharide is chitin.

In some embodiments, and without wishing to be bound to theory or mechanism, the use of a chosen "Second solid phase" biopolymer (or any combination of biopolymers), may offer an added value to the matrix carrier composition, which may be dictated by the intrinsic properties of the biopolymer. For example, the biopolymer may be used to target the matrix carrier composition to a target area and/or to allow the access of the matrix carrier to a required location. For example, mannitol, which is known to cross the blood-brain barrier (BBB) may be used in the matrix composition, to assist the carrier in crossing that barrier. For example, the biopolymer may have intrinsic beneficial activity that may augment or enhance the beneficial activity of the reagent in the carrier. For example, beta glucan, such as, Lentinan, is known to have beneficial effect on the immune system.

According to some embodiments, "Second solid phase" biopolymer may be a structural protein. As used herein, "structural protein" refers to a protein, which may be a biopolymer, and is included for the structure it confers to the particulate matter. In some embodiments, the term refers to a protein, which may be a biopolymer, that confers structure to a cell, cellular membrane, or extracellular membrane in vivo. In some embodiments, the structural protein lacks therapeutic, pharmacologic, pharmaceutical, and/or biological activity whereas in other embodiments the structural protein has an additional therapeutic activity. In embodiments wherein the structural protein has therapeutic activity, the pharmaceutical agent, in some embodiments, is different from the structural protein.

In some embodiments, the structural protein comprises both hydrophilic and hydrophobic residues. In some embodiments, those residues interact with the hydrophobic and/or hydrophilic regions, respectively, of the pharmaceutical agent and/or the "Second solid phase" biopolymer and/or the "First solid phase" nanoparticle.

In some embodiments, the structural protein comprises a high molecular weight (MW) structural protein. In some embodiments, the mean MW of the structural protein is at least 100 kilodalton (kDa). In some embodiments, the mean MW is at least 150 kDa. In some embodiments, the mean MW is at least 200 kDa. In some embodiments, the mean MW is at least 300 kDa. In some embodiments, the mean MW is at least 400 kDa. In some embodiments, the mean MW is at least 500 kDa. In some embodiments, the mean MW is at least 600 kDa. In some embodiments, the mean MW is at least 800 kDa. In some embodiments, the mean MW is at least 1000 kDa. In some embodiments, the mean MW is from 100 to 1000 kDa. In some embodiments, the mean MW is from 150 to 1000 kDa. In some embodiments, the mean MW is from 200 to 1000 kDa. In some embodiments, the mean MW is from 100 to 800 kDa. In some embodiments, the mean MW is from 100 to 600 kDa.

In some embodiments, the structural protein has a Tm under 400° C. Tm may be determined using standard techniques known in the art for analyzing the melting temperatures of proteins.

In some embodiments, the structural protein comprises a fibrous protein. In some embodiments, the structural protein comprises a scleroprotein. In some embodiments, the structural protein is selected from elastin, collagen, keratin, and fibrinogen. In some embodiments, the structural protein is any other fibrous protein or scleroprotein known in the art.

In some embodiments, the structural protein comprises elastin. Non-limiting examples of elastin proteins are described, for example, in GenBank Accession numbers NP_031951, NP_786966, and AAC98394. In some embodiments, the elastin is any other elastin known in the art.

In some embodiments, the structural protein comprises collagen. Non-limiting examples of collagen proteins include those encoded by gene symbols COL3A1, COL14A1, COL11A2, COL5A2, COL11A1, COL5A1, COL4A6, COL4A5, COL4A4, COL4A3, COL4A2, COL1A2, COL5A3, COL18A1, COL12A1, COL19A1, COL24A1, COL4A1, and COL2A1. In some embodiments, the collagen is any other collagen known in the art.

In some embodiments, the structural protein comprises keratin. Non-limiting examples of keratin proteins include keratin 18, keratin 14, keratin 3, and keratin 86 (GenBank Accession numbers P05783, P02533, P12035, 043790, respectively. In some embodiments, the keratin is any other keratin known in the art.

In some embodiments, the structural protein comprises fibrinogen. Fibrinogen is a glycoprotein composed of three pairs of polypeptides: two alpha, two beta, and two gamma chains. Non-limiting examples of the fibrinogen alpha, beta, and gamma chains are described, inter alia, in GenBank Accession numbers P02671, P02675, and P02679. In some embodiments, the fibrinogen is any other fibrinogen known in the art.

Oil

The oil may be composed of either one or a plurality of types of oils. In some embodiments, the oil comprises a plurality of oils. In some embodiments, the matrix carrier composition described herein comprises three or more oils. In some embodiments, the matrix carrier composition described herein comprises four or more oils. In some embodiments, the matrix carrier composition described herein comprises more than four oils.

In some embodiments, the at least one oil is liquid. In some embodiments, the at least one oil is selected from solid and liquid oils. In some embodiments, the at least one oil is selected from solid oils.

According to some embodiments, the component has a melting temperature (Tm) of at least 5° C. In some embodiments, the oil comprises a component having a relatively high melting temperature. In some embodiments, the high Tm component is a liquid at room temperature. In some embodiments, the oil is the high Tm component. In some embodiments, the high-Tm component is included in addition to another oil. A non-limiting example of a high-Tm oil is jojoba oil. In some embodiments, the high Tm oil is any other high melting temperature oil known in the art. In some embodiments, the high Tm oil is used as the majority of the oil. Tm may be determined using standard techniques known in the art for analyzing the melting temperatures of proteins.

In some embodiments, the oil comprises at least one lipid. In some embodiments, the oil comprises at least one naturally-occurring lipid.

In some embodiments, the oil comprises one or more naturally-occurring oils. In some embodiments, the oil comprises a mixture of natural vegetable oils. In some embodiments, the oil comprises one or more oils selected from natural vegetable oils and synthetic analogues thereof.

In some embodiments, the mainly non-polar oil may include polar fractions/parts/regions.

In some embodiments, the oil comprises sesame oil. In some embodiments, the oil comprises olive oil. In some embodiments, the oil comprises linseed oil. In some embodiments, the oil comprises evening primrose oil.

In some embodiments, the oil comprises sea buckthorn oil. In some embodiments, the oil is selected from sesame oil, olive oil, linseed oil, palm oil, jojoba oil, silicon oil and sea buckthorn oil. In some embodiments, the oil is selected from sunflower oil, corn oil, soybean oil, jojoba oil, marrow oil, grapeseed oil, hazelnut oil, apricot oil, macadamia oil, palm oil, almond oil, castor oil, and the like, or any combination thereof.

In some embodiments, the oil may be of animal origin, such as, for example, lanolin.

In some embodiments, the oil comprises synthetic oil, for example silicone oil with molecular weight providing optimal viscosity.

In some embodiments, the oil comprises at least one naturally-occurring oil and at least one synthetic oil.

In some embodiments, the oil comprises unsaturated and saturated oils in the ratio providing optimal viscosity.

In some embodiments, the oil comprises a fatty alcohol. In some embodiments, the oil comprises 2-octyldodecanol. In some embodiments, the oil is selected from a fatty acid ester and a phenylsilicone. In some embodiments, the oil is selected from phenyltrimethicones, diphenyldimethicones, and poly-methylphenylsiloxanes.

In some embodiments, an oil component comprises a component capable of stimulating secretion of bile salts or bile acids when ingested by a subject. In some embodiments, the bile-stimulating component is an oil. In some embodiments, the component comprises olive oil or an extract thereof. In some embodiments, the component is any other bile salt/acid stimulating lipid-soluble substance known in the art. In some embodiments, the oil is the bile salt/acid stimulating substance. In some embodiments, the bile salt/acid stimulating substance is a substance separate from the oil.

In some embodiments, the oil may contain at least one anti-oxidant. For example, sea buckthorn (oblepicha) oil contains beta-carotene. In some embodiments, any other oil enriched in at least one anti-oxidant may be used. In some embodiments, any other oil enriched in at least one vitamin may be used. Non-limiting examples are Vitamin A, Vitamin E, beta-carotene, Vitamin D or any combination thereof.

In some embodiments, the oil may be another suitable oil known in the art.

In some embodiments, the matrix carrier composition comprises an additional oil component. The additional oil component may comprise an additional oil or mixture of oils. In some embodiments, the oil of the additional oil component is olive oil. In some embodiments, the oil is another suitable oil known in the art.

In some embodiments, the additional oil component further comprises an antioxidant.

In some embodiments, the additional oil, or mixture of oils may have a higher viscosity than the first-added oil or mixture of oils.

In some embodiments, the matrix carrier composition further comprises a third oil or mixture of oils in addition to the above-described additional oil component. In some embodiments, the third oil component comprises an antioxidant.

In some embodiments, the third oil component comprises sesame oil. In some embodiments, the third oil component is another suitable oil known in the art.

In some embodiments, the third oil, oil or mixture of oils may have a higher viscosity than the additional oil or mixture of oils. Not limiting example for a third oil is a palm oil.

In some embodiments, the at least one oil comprises at least one wax. In some embodiments, the wax is a substance having the following properties: (a) plastic (malleable) at normal ambient temperature; (b) having a melting point above approximately 45° C. (113° F.); (c) a low viscosity when melted, relative to a typical plastics; (d) insoluble in water; and (e) hydrophobic. In some embodiments, the wax is a natural wax, for example bees wax, a wax derived from plant material, or a synthetic wax prepared by esterification of a fatty acid and a long chain alcohol. Other suitable waxes include petroleum waxes such as a paraffin wax.

Use of the Matrix Carrier Composition

The matrix carrier compositions described herein may be combined with one or more pharmaceutical agents, as described below, to produce a pharmaceutical composition/delivery system, suitable for administration. Administration may include any type of administration, such as, for example, oral administration, parenteral administration, topical administration, and the like.

In some embodiments, oral administration of the pharmaceutical compositions described herein results in enhanced potency of the pharmaceutical agent as compared to oral administration of the pharmaceutical agent alone. In some embodiments, oral administration of the pharmaceutical compositions described herein results in at least comparable, if not enhanced, potency of the pharmaceutical agent as compared to non-oral administration of the pharmaceutical agent. In some embodiments, oral administration of the pharmaceutical composition described herein provides an increase in potency by, for example, extending the pharmaceutical agent's life time in blood, improving the pharmaceutical agent's targeting ability, and/or decreasing the pharmaceutical agent's side effects, as compared to the drug when orally administered alone.

In some embodiments, the relative potency of the pharmaceutical agent when administered orally as part of the pharmaceutical compositions described herein is at least 20% higher than the relative potency of the pharmaceutical agent when orally administered alone; alternatively, at least 50% higher; alternatively, at least 2 times higher; alternatively, at least 3 times higher; alternatively at least 4 times higher; alternatively, at least 5 times higher; alternatively, at least 10 times higher; alternatively, more than 10 times higher.

In some embodiments, the ADME profile of the pharmaceutical agent when administered orally as part of the pharmaceutical compositions described herein is altered as compared to the ADME profile of the pharmaceutical agent when orally administered alone.

In some embodiments, the oral administration of the pharmaceutical compositions described herein results in enhanced oral bioavailability of the pharmaceutical agent as compared to oral administration of the pharmaceutical agent alone. In some embodiments, the relative oral bioavailability of the pharmaceutical agent when administered as part of the pharmaceutical compositions described herein is at least 10% higher than the relative oral bioavailability of the pharmaceutical agent when orally administered alone; alternatively, at least 20% higher; alternatively, at least 50% higher; alternatively, at least 60% higher; alternatively, at least 70% higher; alternatively, at least 80% higher. In some embodiments, the relative oral bioavailability of the pharmaceutical agent when administered as part of the pharmaceutical compositions described herein is at least two times higher than the relative oral bioavailability of the pharmaceutical agent when orally administered alone; alternatively, at least three times higher; alternatively at least four times higher; alternatively, at least five times higher; alternatively, at least ten times higher; alternatively, more than ten times higher.

In some embodiments, oral administration of the pharmaceutical composition described herein may result in improved targeting and/or specificity of the pharmaceutical agent as compared to oral administration of the active ingredient alone. Such targeting and specificity, in some embodiments, may be further improved through the use of one or more enhancers, as discussed herein, as part of the pharmaceutical composition described herein.

In some embodiments, the oral administration of the pharmaceutical compositions described herein results in increased half life in plasma or the lymph circulation of the pharmaceutical agent as compared with oral administration alone. It is to be understood, that the ability to increase the half-life of the pharmaceutical agent by using the pharmaceutical compositions described herein may be independent of the pharmaceutical agent's oral bioavailability. The pharmaceutical compositions described herein, when administered orally, may be used to increase half-life of poorly as well as highly orally bioavailable drugs. In some embodiments, the half-life of the pharmaceutical agent in the pharmaceutical compositions described herein, when administered orally, is at least 10% higher than the half-life of the pharmaceutical agent when orally administered alone; alternatively, at least 20% higher; alternatively at least 30% higher; alternatively, at least 40% higher; alternatively, at least 50% higher; alternatively, at least 60% higher; alternatively, at least 70% higher; alternatively, at least 80% higher; alternatively, at least 90% higher; alternatively, at least 2 times higher; alternatively at least 3 times higher.

In some embodiments, oral administration of the pharmaceutical composition described herein may result in a more controlled lifetime of the pharmaceutical agent in the blood and lymph circulation as compared to administration of the pharmaceutical agent by injection or inhalation.

In some embodiments, oral administration of the pharmaceutical composition described herein may not result in a high initial concentration peak upon administration as compared with that found from injected or inhaled formulations of the same pharmaceutical agent. Such high concentration may lead to side effects such as immune response and inflammation process, similar to hematoma.

In some embodiments, oral administration of the pharmaceutical composition described herein may result in a slower release profile of the active reagent in the blood as compared to oral administration of the active ingredient alone.

In some embodiments, oral administration of the pharmaceutical composition described herein may result in decreased side effects or allergic reactions, even when administered orally at order of magnitude higher daily doses, as compared to oral administration of the pharmaceutical agent alone. Such decrease may be in the number of patients reporting the side effects or allergic reactions or in the severity of the side effects or allergic reactions.

In some embodiments, oral administration of the pharmaceutical composition described herein may result in the ability to treat diseases and conditions that otherwise would not be treatable with the same pharmaceutical agent when orally administered alone. In some embodiments, oral administration of the pharmaceutical composition described herein may result in an improved ability to treat diseases and conditions than when the pharmaceutical agent is administered alone in a way other than orally, such as by intravenous or inhalation administration.

In some embodiments, oral administration of the pharmaceutical composition described herein may result in the use of a lower dose (amount) of the pharmaceutical agent to achieve a certain effect as compared to the dose (amount) of pharmaceutical agent required to achieve that same effect when administered orally alone or when administered alone by a way other than orally.

In some embodiments, oral administration of the pharmaceutical composition described herein may result in different biodistribution, (that is, the distribution in various tissues and organs) as compared to the biodistribution of the pharmaceutical agent when administered orally alone or when administered alone by parenteral route.

Provided is a pharmaceutical composition comprising an intermolecular association of at least one pharmaceutical agent, at least one biopolymer, nanoparticles, and at least one oil.

In some embodiments, the pharmaceutical composition is anhydrous. In some embodiments, the composition is preferably in the absence of water and surfactants.

In some embodiments, the pharmaceutical composition is formulated in a form suitable for oral delivery using conventional methods known in the art. In some embodiments, the form is selected from capsules (including soft gel capsules, hard gelatin capsules), tablets (including coated tablets, pressured tablets), liquid form (including solutions and suspensions), jell form, liquid form coated by jell or hard phase, pastes, and the like, or any combination thereof. In some embodiments, the pharmaceutical composition may be formulated in the form of small or micro-droplets impregnated into biocompatible soluble porous nutritional material like agar, fruit jelly, cornflex, etc or into any biocompatible water based gel.

In some embodiments, parenteral administration of the pharmaceutical compositions described herein may be used. The parenteral administration may be used in patients with any gastrointestinal problem, swallowing difficulties or in accordance with the patient preference or medical decision. The parenteral use of the pharmaceutical agent with the pharmaceutical compositions described herein, may result in different pharmacodynamic and/or pharmacokinetics profile, as compared to the parenteral administration of the pharmaceutical agents without the matrix carrier of the invention.

Pharmaceutical Agent

In some embodiments, the matrix carrier compositions described herein may be combined with one or more pharmaceutical agents. In some embodiments, the one or more pharmaceutical agents may exhibit a non-covalent interaction with the matrix carrier composition, or one or more components thereof. In some embodiments, the one or more pharmaceutical agents is covalently bonded to one or more of the components of the matrix carrier composition.

In some embodiments, the pharmaceutical agent comprises one or more compounds with poor oral bioavailability. In some embodiments, the pharmaceutical agent is poorly absorbed or not absorbed at all from the gastrointestinal tract or gut. In some embodiments, the pharmaceutical agent has poor water solubility and/or slow dissolution rate.

In some embodiments, the pharmaceutical agent is a drug agent, which has a short half life (t½) in plasma. In some embodiments, the pharmaceutical agent is a drug with plasma half-life shorter than 10 hours; alternatively, a drug with plasma half-life shorter than 8 hours; alternatively, a drug with plasma half-life shorter than six hours; alternatively, a drug with plasma half-life shorter than four hours; alternatively, a drug with plasma half-life shorter than three hours; alternatively, a drug with plasma half-life shorter than two hours.

In some embodiments, the one or more pharmaceutical agents are poorly water-soluble and in a crystalline, semi-crystalline, amorphous state, or combination of such states.

In some embodiments, the pharmaceutical agent is branched in structure.

In some embodiments, the pharmaceutical agent is substantially hydrophobic.

In some embodiments, the pharmaceutical agent is substantially hydrophilic.

In some embodiments, the one or more pharmaceutical agents are water-soluble.

In some embodiments, the pharmaceutical composition comprises more than one pharmaceutical agent.

In some embodiments, the pharmaceutical agent may include a nutritional agent or a combination of nutritional agents. The term "pharmaceutical drug" is intended to include substances having pharmacological and/or pharmaceutical, and/or biological activity.

Additional Components

According to some embodiments, the matrix carrier composition may further include one or more additional components that may be used to enhance the effect achieved by the use of the matrix carrier composition and provide an added value to the matrix. In embodiments wherein the one or more additional components is an enhancer, as discussed below, that enhancer may be associated with the matrix carrier composition. For example, the additional component(s) may have structural effect, beneficial therapeutic effect (that may be synergistic to the active reagent of the matrix), targeting effect, allow better control of the pharmacokinetics of the compositions, and the like, or any combination thereof. The additional components may include any type of natural occurring molecules, synthetic molecules, or combinations thereof. For example, various amino acids (such as, for example, but not limited to Arginine, Histamine, Aspartate, Glutamate, and the like), may be used in the composition, as a targeting enhancer. For example, molecules isolated from natural sources may be used in order to provide added therapeutic value to the active reagent in the matrix. For example, the additional components may include extracts of various natural sources. Natural sources may include, for example, mushrooms, such as, for example, medicinal mushrooms, cordiceps mushrooms, plants, animals and the like. Exemplary molecules isolated from mushrooms may include such components as, but not limited to: polysaccharides, such as, for example, beta-glucans which stimulate the innate branch of the immune system. beta-glucans have been shown to have the ability to stimulate macrophage, NK cells, T cells and the production of immune system cytokines; antioxidants such as, for example, but not limited to ascorbic acid, tocopherols, phenolic compounds, and carotenoids; alpha-glucosidase inhibitor, which have a beneficial effect on blood sugar levels; anticholesterol compounds, such as, for example, eritadenine, lovastatin, and the like; molecules having anti hormone activity; vitamin D2; Molecules having antiviral, antibacterial, and/or antifungal properties; molecules having anti-cancer effect, such as, for example, polysaccharide compounds isolated from maitake mushroom. Molecules isolated from plants may include such molecules as, but not limited to polyphenols, which are characterized by the presence of more than one phenol unit or building block per molecule. Polyphenols are generally divided into hydrolyzable tannins (gallic acid esters of glucose and other sugars) and phenylpropanoids, such as lignins, flavonoids, and condensed tannins and may have antioxidant activity. In some embodiments, the additional component may include an isolated molecule, an isolated fraction or an extract of a cordiceps molecule. In some embodiments, the additional component may include any type of Glucagon like peptide (GLP), such as, GLP-1, GLP-2, or analogs thereof. Glucagon-like peptide is derived from the transcription product of the proglucagon gene. The major source of GLP in the body is the intestinal L cell that secretes GLP as a gut hormone. GLP-1 secretion by L cells is dependent on the presence of nutrients in the lumen of the small intestine. Physiological roles of GLP include: increasing insulin secretion from the pancreas in a glucose-dependent manner; decreasing glucagon secretion from the pancreas; increasing beta cells mass and insulin gene expression; inhibiting acid secretion and gastric emptying in the stomach; decreasing food intake; promoting insulin sensitivity. In some embodiments and without wishing to be bound to mechanism or theory, the GLP in the matrix provides a structural effect by stabilizing the matrix structure. In addition, the GLP provides an added beneficial effect (for example, when used in a matrix carrier composition which includes insulin as a protein reagent) by providing additional means of controlling blood sugar level, and by preventing ulcer. Furthermore, the use of GLP in the matrix carrier composition may aid in targeting the matrix carrier.

In some embodiments, the matrix carrier composition and/or the pharmaceutical composition further comprises at least one antioxidant. In some embodiments, the at least one antioxidant may include, but not limited to vitamin E, superoxide dismutase (SOD), catalase, glutation peroxidase, N-acetylcysteine, Vitamin A, Vitamin D, Vitamin C, omega-3, and beta-carotene.

In some embodiments, substantially anhydrous matrix carrier pharmaceutical composition may include molecules and/or particles having hydrophilic properties. Non limiting examples are hydrophilic silica, water soluble vitamins, and the like.

In some embodiments, the matrix carrier composition and/or the pharmaceutical composition further comprises at least one pharmaceutical-grade surfactant. Surfactants are well known in the art, and are described, inter alia, in the Handbook of Pharmaceutical Excipients (eds. Raymond C Rowe, Paul J Sheskey, and Sian C Owen, copyright Pharmaceutical Press, 2005). In some embodiments, the at least one surfactant is any other surfactant known in the art. Emulsifiers and emulgators, each being examples of surfactants, are well known in the art, and are described, inter alia, in the Handbook of Pharmaceutical Excipients (ibid). Non-limiting examples of emulsifiers and emulgators are eumulgin, Eumulgin B1 PH, Eumulgin B2 PH, hydrogenated castor oil cetostearyl alcohol, and cetyl alcohol. In some embodiments, the emulsifier or emulgator is any other emulsifier or emulgator known in the art.

In some embodiments, the matrix carrier composition and/or the pharmaceutical composition further comprises at least one pharmaceutical-grade stabilizer. Stabilizers are well known in the art, and are described, inter alia, in the Handbook of Pharmaceutical Excipients (ibid). In some embodiments, the at least one stabilizer is any other stabilizer known in the art.

According to some embodiments, the matrix carrier composition and/or pharmaceutical composition may further include an enhancer and/or targeting component.

The term "Enhancer" refers to any substance that directly or non-directly enhances biological and/or pharmacological potency of the pharmaceutical agent. Non limiting examples of enhancers include, but not limited to: omega-3, beta-caroten, bioflavanoid, biotin, antioxidant, amino acid, SOD, catalase, salts of microelements, and the like, or any combination thereof. For example, beta glucan, such as, Lentinan, is known to have beneficial effect on the immune system and may be used as enhancer.

The term "Targeting component"—refers to any substance that can improve targeting and/or bio-distribution of the pharmaceutical agent to a desired spatial location. The targeting component may include any targeting agent known in the art, that may be used to target the pharmaceutical agent to the desired spatial location. For example, the targeting component may include such components as, but not limited to: Specific antibodies; Specific polysaccharides; Positively and/or negatively charged amino acids and/or polysaccharides; Small molecules which have increased affinity to specific receptors on the tumor cell membrane and/or organelle; Short peptides; antagonist receptor, and the like, or any combination thereof. In some embodiments, the targeting enhancer is chosen from positively charged amino acids, such as lysine, arginine, histidine, aspartate and glutamate. In some embodiments, the enhancer is a sugar alcohol. In some embodiments, the targeting component is selected from mannitol and xylitol. Non limiting examples of targeting agents include, but not limited to: mannitol (that may improve blood brain barrier penetration), amino acid, antibodies, and the like, or any combination thereof.

In some embodiments, metals, metalloproteins, electrolytes, or any combination thereof, may be used as targeting enhancers to aid in targeting the pharmaceutical agents to a desired spatial location, based on local environment, in that location. The targeting enhancers may be added at different steps of production, depending on their properties and the desired action. The local environment may include such parameters as, but not limited to: local acidity, local temperature, local concentration of the pharmaceutical agent, membrane potential distribution, or any combination thereof.

In some embodiments, the enhancer is selected from: bioflavanoids, heat shock proteins, microelements and the like.

According to some embodiments, the pharmaceutical composition may include more than one pharmaceutical agent with one or more enhancers and/or targeting components, or any combination thereof. Each possibility represents a separate embodiment of the present invention.

In some embodiments, the matrix carrier composition and/or the pharmaceutical composition may further comprise at least one enhancer of the therapeutic activity of the pharmaceutical agent. In some embodiments, the matrix carrier composition and/or the pharmaceutical composition further comprises at least one cofactor.

In some embodiments, as understood by those of skill in the art, an enhancer may exhibit therapeutic activity. That is, in some embodiments, an enhancer may serve a dual function, namely as a pharmaceutical agent in its own right and as an agent that enhances the activity of a different pharmaceutical agent.

In some embodiments, the matrix carrier composition and/or the pharmaceutical composition further comprises at least one amino acid selected from arginine, lysine, aspartate, glutamate, and histidine. In some embodiments, analogues and modified versions of arginine, lysine, aspartate, glutamate and histidine are included in the terms "arginine," "lysine," "aspartate", "glutamate" and "histidine," respectively. In some embodiments, the at least one amino acid promotes interaction of the pharmaceutical agent with a target cell.

In some embodiments, the at least one excipient provides a desired taste to the pharmaceutical composition. In some embodiments, the at least one excipient influences the drug consistency, and the final dosage form such as a gel capsule, hard gelatin capsule, tablet or soft gel.

Non limiting examples of excipients include:

Antifoaming agents (dimethicone, simethicone);

Antimicrobial preservatives (benzalkonium chloride, benzelthonium chloride, butylparaben, cetylpyridinium chloride, chlorobutanol, chlorocresol, cresol, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol);

Chelating agents (edetate disodium, ethylenediaminetetraacetic acid and salts, edetic acid);

Coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein);

Colorants (caramel, red, yellow, black or blends, ferric oxide);

Complexing agents (ethylenediaminetetraacetic acid and salts (EDTA), edetic acid, gentisic acid ethanolmaide, oxyquinoline sulfate);

Desiccants (calcium chloride, calcium sulfate, silicon dioxide);

Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax);

Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin);

Humectants (glycerin, hexylene glycol, propylene glycol, sorbitol);

Polymers (e.g., cellulose acetate, alkyl celluloses, hydroxyalkylcelluloses, acrylic polymers and copolymers);

Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methyl cellulose, pectin, polyethylene oxide, polyvinyl alcohol, povidone, propylene glycol alginate, silicon dioxide, colloidal silicon dioxide, sodium alginate, tragacanth, xanthan gum);

Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); or any combination thereof.

This list is not meant to be exclusive, but to be merely representative of the classes of excipients and the kinds of excipients which may be used in oral pharmaceutical compositions described herein.

Methods of Manufacturing of Matrix Carrier Compositions

According to some embodiments, there are provided methods of manufacturing the matrix carrier composition described herein. In some embodiments, the method, intended to illustrate the disclosure and without however limiting the scope thereof, comprises at least some of the following steps:

1. Activation of the second solid phase surface of the matrix-carrier by additional milling, vacuum treatment, chemical or ultra-sound cleaning or reduction.
2. Mixing biopolymers with liquid oils under vacuum or in inert atmosphere.
3. Inserting nanoparticles into oils and optional additional vacuum treatment for removing air from the nanoparticles surface
4. Inserting pharmaceutical agent(s) into pure oils, oils with hydrophobic nanoparticles or oils with biopolymers, with or without silica, depending on physical properties (such as hydrophobicity) of the pharmaceutical agent.
5. Mixing and homogenization of the system may take into consideration the sensitivity of the pharmaceutical agent to mechanical stress. This process maybe performed under inert atmosphere with control of temperature, rate and time. The homogenization may decrease the viscosity and promote packing.

The "maturation" of the matrix carrier composition may be achieved by maintaining under controlled temperature (for example, in the range of about 1-37° C.) for 1-72 hours with or without inert atmosphere.

According to some embodiments, the order of manufacturing steps may depend on the specific equipment used and the properties of the pharmaceutical agent and may be changed accordingly.

In other embodiments, the method, intended to illustrate the disclosure and without however limiting the scope thereof, comprises:

mixing in at least one oil, nanoparticles, and at least one biopolymer, whereby an intermolecular association of the at least one biopolymer, the nanoparticles, and the at least one oil is formed.

In some embodiments, the method of manufacturing the matrix carrier composition, intended to illustrate the disclosure and without however limiting the scope thereof, comprises:

a) combining nanoparticles with at least one biopolymer; and b) blending the combination into at least one oil, whereby an intermolecular association of the at least one biopolymer, the nanoparticles, and the at least one oil is formed.

In some embodiments the mixing may involve dry mixing. In embodiments involving dry mixing, combining the nanoparticles with at least one biopolymer further comprises the step of confirming that the combination is properly homogenized. In some embodiments, any of the following three tests are utilized, it being sufficient for determining proper homogenization if a positive result is obtained in any of the three tests, even though one or more of the other tests may not produce a positive result: (a) the mixture appears homogenous; (b) the volume of the mixture is smaller than the sum of volumes of the two components; and (c) the mixture does not sink when placed on the surface of a still body of water. Should the combination fail to meet any of those three criteria, then, in some embodiments, the method further comprises adding additional nanoparticles or a hydrophobic agent to the mixture. These steps are repeated until the combination meets at least one of the above criteria.

In some embodiments, the method of manufacturing the matrix carrier composition, intended to illustrate the disclosure and without however limiting the scope thereof, comprises the steps of:
  a) combining nanoparticles, at least one biopolymer and at least one structural protein; and
  b) blending the combination into at least one oil
whereby an intermolecular association of the at least one biopolymer, the nanoparticles, the at least one structural protein, and the at least one oil is formed.

Also provided are methods of manufacturing the pharmaceutical compositions described herein.

In some embodiments, the method of manufacturing the pharmaceutical compositions comprises the steps of:
  (a) providing a matrix carrier composition;
  (b) mixing at least one pharmaceutical agent with at least one oil; and
  (c) combining the matrix carrier composition with the mixture of the pharmaceutical agent with the at least one oil.

In some embodiments, the method of manufacturing the pharmaceutical compositions comprises the steps of:
  (a) mixing nanoparticles with at least one biopolymer;
  (b) mixing at least one pharmaceutical agent with at least one oil; and
  (c) combining the mixture of nanoparticles and the at least one biopolymer with the mixture of the pharmaceutical agent with the at least one oil.

In some embodiments, the method of manufacturing the pharmaceutical compositions comprises the steps of:
  (a) mixing at least one biopolymer with at least one oil;
  (b) mixing nanoparticles with at least one oil;
  (c) combining the mixture of nanoparticles and the at least one biopolymer with the mixture of the pharmaceutical agent with the at least one oil.

In some embodiments, the methods of manufacturing the pharmaceutical compositions described herein further comprise:
  Formulating the pharmaceutical composition a form suitable for oral delivery.

It is within the knowledge of a skilled artisan that the order of mixing and the order of addition of the individual components can be modified to meet any specific needs.

In some embodiments, inert gas, such as, for example, $N_2$ or $CO_2$, may be used in the manufacturing process, to prevent oxidation of the at least one oil (or one or more other components) during the manufacturing process. The manufacturing process may be conducted in a closed reactor having an internal impeller. In this reactor, $N_2$ and/or $CO_2$ may be supplied.

In some embodiments, a high shear mixer is used. In some embodiments, other means suitable for generating a homogenous formulation, as defined above, from the nanoparticles and the at least one biopolymer is used.

In some embodiments, the method further comprises suspending the matrix carrier composition in at least one oil until homogenous distribution, as defined above, of the solid phase is achieved using the airlift or boiling layer technologies. The oil used in preparing the suspension may be the same as or different from the at least one oil used in preparing the matrix carrier composition.

The airlift technology involves the insertion of gas bubbles into a liquid composition. The bubble flow efficiently mixes the liquids and/or suspensions and may facilitate particle interaction and/or adsorption. Specifically, the bubble surface adsorbs the different particles and generates shock waves during bubble destruction. This gas "boiling layer" forms flying micro-drops and/or particles in the arising flow of the gas above the liquid surface. Micro-drops may be created by sprinkler with or without an ultrasound transducer. The boiling layer improves the interaction of the particles and the liquid (oil) drops due to increased frequency and energy of collisions.

In some embodiments, the biopolymer may undergo dry milling/grounding before use. In some embodiments, decreasing the particle size of the biopolymer (e.g., in order to improve homogeneity) to sizes of, for example, less than 10 μm may be achieved by homogenization of the biopolymer in the at least one oil prior to addition of the nanoparticles. In some embodiments, vacuum methods may be used to remove moisture and air from the biopolymer and/or lyophilized pharmaceutical agent mix (in oil or without oil).

In some embodiments, in order to improve adsorption, the biopolymer and nanoparticles surface is released from air micro-bubbles and small water droplets. This may be achieved by vacuum drying and gas removal or/and drying by passing of drying agent (such as, for example, gases like $N_2$, $CO_2$, He or other inert gases) through the mix. Gas removal may also be performed by centrifugation or/and deep vacuum.

In some embodiments, the method of manufacturing a matrix carrier composition further comprises the step of adding additional oil following the addition of the at least one oil. The term "additional oil" encompasses an oil or mixture of oils, as described elsewhere herein. In some embodiments, the additional oil, oil or mixture of oils has a higher viscosity than the first-added oil or mixture of oils. In some embodiments, without wishing to be bound by any theory or mechanism of action, the use of a higher viscosity oil or oil mixture at this stage can enable formation of ordered structures in the composition.

In some embodiments, the method of manufacturing a matrix carrier composition further comprises the step of adding a third oil or mixture of oils after addition of the above-described at least one oil.

In some embodiments, the at least one oil comprises at least one wax. In some embodiments, the at least one wax is heated. In some embodiments, the at least one wax is pulverized. In some embodiments, the at least one wax is both heated and pulverized. In some embodiments, the heating and/or pulverization are performed prior to blending with the other components. In some embodiments, the at least one wax remains hot while blending with the other components begins. In some embodiments, the heating and/or pulverization are performed during blending with the other components. In some embodiments, the heating and/or pulverization are performed both prior to and during blending with the other components.

In some embodiments, wax may further be used as an additional stabilizing rheological component. Wax has no hydrophilic surface and has internal energy which is lower than the internal energy of polysaccharides and silica. Low internal energy of wax is related to the low melting point of wax. High melting point may deactivate/denaturate the pharmaceutical agent during the manufacturing process of the composition. To this aim, eutectic mix with lower melting temperature between may be prepared by premixing the wax with additional wax or oil having high thermal stability. Use of the eutectic mix of wax and oil with the pharmaceutical agent mix, while mixing gently (for example, at about 2000-2500 rpm), enables cooling of eutectic mix and thus a solid and a liquid disperse phases are formed. Such a process may further enable the formation of small solid wax droplets. Without wishing to be bound by any theory of mechanism of action, when such small solid fat droplet are formed, then these droplets, after administration, will not be digested by lipases and would go to feces, and hence the effective ratio of the anti-cancer reagent penetration will be increased relatively to liquid composition without wax and the additional solid phase. The choice of type of wax with a desired predetermined melting point and its final concentration as well as method of its insertion in the formulation enables the to regulate the dispersion as well as stability and consistence of the final formulation.

The oil or mixture of oils used for each pharmaceutical agent may be the same or different.

In some embodiments, two or more different pharmaceutical agents may be combined within a single mixture of nanoparticles associated with the biopolymer and then mixed with the oil components.

In some embodiments two or more pharmaceutical agents may be individually combined with the nanoparticles associated with the biopolymer and then these individual mixtures may be further mixed together with the oil components.

In some embodiments, the step of mixing a pharmaceutical agent with at least one oil comprises the step of directly dissolving the pharmaceutical agent into the at least one oil. In some embodiments, a solution of the pharmaceutical agent in a solvent, such as water, is mixed with the at least one oil and the solvent is then removed. In some embodiments a solution of the pharmaceutical agent may be lyophilized previously to being added to oil.

In some embodiments, the pharmaceutical agent forms a suspension when mixed with the at least one oil. In some embodiments, the pharmaceutical agent is dissolved in the at least one oil.

In some embodiments, the pharmaceutical agent is mixed with the at least one oil in the presence of an alcohol.

In some embodiments, the pharmaceutical agent is mixed with the at least one oil in the presence of polyethylene glycol present. In some embodiments the polyethylene glycol has a molecular weight in the 200-8000 dalton range.

In some embodiments the pharmaceutical agent is mixed with the at least one oil in the presence of perfluorocarbon. In some embodiments the perfluorocarbon is a liquid at room temperature.

In some embodiments, the pharmaceutical agent is mixed with the at least one oil under anhydrous conditions. In some embodiments, moisture is present. In some embodiments, an aqueous solution of the pharmaceutical agent is mixed with the at least one oil.

In some embodiments the pharmaceutical agent may be dissolved in oil and stay there for 10-48 hours or more previously to formulation preparation.

In some embodiments, a combination of several pharmaceutical agents may be formulated into one formulation. In some embodiments, preparation of particulate matter comprising each pharmaceutical agent is done separately and at the last step, the separate particulate matters are put together without additional mixing. Several technologies may be used to prevent comparative adsorption of the pharmaceutical agents on the solid phase as well as chemical interaction between them: the pharmaceutical agents are each formulated in a jell (non liquid formulation) or with any bioavailable solidifications; the pharmaceutical agent formulations may be prepared as a mix of small drops or particles from practically solid materials (at room temperature) and/or suspension in liquid lipid phase of solid or semi-solid balls and/or pieces with pharmaceutical agents.

In some embodiments, the formulation method of pharmaceutical agents including association of the pharmaceutical agents with the biopolymer and/or nanoparticle may be performed, for example, by the "Sandwich" technology (the "sandwich" technology provides a formation of multilayer structure which consists of consequently adsorbed components. Thus, the process provides sequential spatial and temporal adsorption with predetermined properties) Exposure may be performed for 30 min-72 hours depending on the pharmaceutical agent and the therapy needs (which may effect PK and PD). Further mixing with other ingredients may be preformed, for example: for preliminary adsorption 0 to 100% of nanoparticles or biopolymers may be used, according to required PK and PD. Adsorption activity of nanoparticles and/or biopolymers may be achieved by preliminary treatment in homogenizer and/or by ultra-sound. For some pharmaceutical agents, colloidal metals, such as, for example, Zn, Cu, Fe, and the like, may be used as structure forming element. Controlled electrolysis with further lyophilization or vacuum drying may be used to implement the colloidal metals in the formulation.

Also provided are products of the manufacturing processes described herein.

According to further embodiments, and as shown in Example 7, in order to extract the pharmaceutical agent from the matrix carrier composition into a solution, an extracting procedure should be used. The use of such extraction procedures is indicative that the pharmaceutical agent is held in the matrix carrier in a complex by non-covalent forces and therefore the use of an organic solvent and surfactant are necessary in order to extract said agent from the matrix.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

EXAMPLES

The following examples are intended to illustrate the disclosure and without however limiting the scope thereof.

Example 1

Matrix Carrier Pharmaceutical Composition Preparation—General Protocol No. 1

The following process may be used to prepare pharmaceutical compositions as described herein.

Step 1. Add pharmaceutical agent to at least one oil. Optionally, hold in refrigerator for 12-72 hours.
Step 2. Mix and/or homogenize biopolymer and silica into oils.
Step 3. Vacuum may be used for removing adsorbed gases.
Step 4. Continue mixing.
Step 5. Add enhancers, continue mixing.
Step 6. Packaging the formulation of step 5.

Example 2

Matrix Carrier Pharmaceutical Composition Preparation—General Protocol No. 2

The following process may be used to prepare pharmaceutical compositions as described herein.
Step 1. Optional dry milling of one or more biopolymers together (additional dry mixing).
Step 2: Insertion of part of the biopolymer mixture into an oil, mixing; insertion of part of silica, mixing and continue adding one after another until all of the silica and the biopolymers are incorporated.
Step 3. Vacuum with mixing for to remove gases.
Step 4. Addition of pharmaceutical agent, mixing.
Step 5. Optionally addition of enhancers, additional components, mixing.
Step 6. Packaging the formulation of step 5.

Example 3

Matrix Carrier Pharmaceutical Composition Preparation—General Protocol No. 3

The following process may be used to prepare pharmaceutical compositions as described herein.
Step 1. Inserting hydrophobic silica nanoparticles and polysaccharides (or mixture of the polysaccharides) into lipid or mix of lipids (oils) such as by using airlift with inert gases or boiling layer technologies and mixing vigorously by shearing mixer or homogenizer until an homogenous distributed oil based suspension is obtained.
Step 2. Adding the pharmaceutical agent into the lipid/oil based suspension of step 1; it is important to control the temperature, intensity of mixing, and the oxidative properties of the gas phase of the reactor in which the mixing is performed.
Step 3. Mixing the oil based suspension of step 2 until homogenous distributed oil suspension is obtained.
Step 4. Adding a targeting and/or enhancer component, such as, arginine; vitamins or co-enzymes to the homogenous distributed oil based suspension of step 3, and gently mixing with inert material agitator under inert atmosphere.
Step 5. Adding while mixing, an additional oil, such as palm oil, and/or wax for physical stabilization of the formulation.
Step 6. Packing the formulation of step 5.

Example 4

Matrix Carrier Pharmaceutical Composition Preparation—General Protocol No. 4

The following process may be used to prepare pharmaceutical compositions as described herein.
Step 1. Dry mixing the hydrophobic silica nanoparticles and polysaccharides or mix of the polysaccharides in a reactor with liquid or gas dynamic sealing (sealing with controlled leakage of the working medium provides protection of the bearing, valves and surroundings from contamination by aerosol and nanoparticles). Dry mixing may be performed by an agitator with protected blades, or by gas using a boiling layer technology.
Step 2. Inserting a pharmaceutical agent into lipids, oil or mix of oils.
Step 3. Mixing gently the lipid based suspension of steps 2 and the powder of silica nanoparticles and polysaccharide of step 1, until homogenous distribution of the solid phase is achieved.
Step 4. Adding a targeting and/or enhancer component, such as, arginine; vitamins or co-enzymes to the homogenous distributed oil based suspension of step 3, and gently mixing with inert material agitator under inert atmosphere.
Step 5. Adding while mixing, an additional oil, such as palm oil, and/or wax for physical stabilization of the formulation.
Step 6. Packing the formulation of step 5.

Example 5

Matrix Carrier Pharmaceutical Composition Preparation—General Protocol No. 5

The following process may be used to prepare pharmaceutical compositions as described herein.
1. Activation of the second solid phase surface of the matrix-carrier by additional milling, vacuum treatment, chemical or ultra-sound cleaning or reduction.
2. Mixing activated biopolymers (such as polysaccharides) with liquid oils under vacuum or in inert atmosphere.
3. Inserting nanoparticles into oils and additional vacuum treatment for removing air from particles surface
4. Inserting pharmaceutical agent(s) into pure oils, oils with hydrophobic nanoparticles or oils with biopolymers with or without silica, depending on the hydrophobicity of the pharmaceutical agent.
5. Mixing and homogenization of the system takes into account sensitivity of the pharmaceutical agents to mechanical stress. This process is provided under inert atmosphere with control of temperature, rate and time treatment.
6. The homogenization allows inserting into the material additional energy which may decreases viscosity of the materials and promote its packing.
7. The maturation of the material may be achieved by maintaining under controlled temperature (in the range of 1-25° C.), for 1-72 hours. The maturation may increase viscosity and energy of binding matrix-carrier with the pharmaceutical agent.

Example 6

Analysis and Comparison of Insulin within or without the Matrix Carrier

LC/MS stability analysis of insulin samples was performed in order to evaluate insulin stability within or without the Matrix Carrier Formulation at different time points (0, 2 weeks, 1 month and 3 months) during storage at 4-5° C. Insulin Bulk row material without the Matrix Carrier Formulation was stored in glass vials. Insulin within the Matrix Carrier Formulation, which composition is detailed in the Example 7, was capsulated into gelatin capsules (Capsugel, size 00). In order to perform HPLC and LC/MS analysis, the samples followed similar extraction procedure as detailed in Example 7 below.

FIG. 1, panel A demonstrate the LC/MS of raw bulk insulin (that is, insulin not within the matrix carrier) after 3 month of storage at 4-5°. FIG. 1, panel B demonstrate the LC/MS of insulin extracted from Matrix Carrier Formulation, after 3 month of storage at 4-5°.

Comparison of the LC/MS spectrums of FIG. 1 panels A and B show that the two spectrums are similar. The results suggest that the Matrix Carrier Formulation does not reduce the stability of the pharmaceutical agent and that the bonds between the pharmaceutical agent (Insulin) and the Matrix Carrier are not covalent.

Example 7

Extraction of Pharmaceutical Agent from the Matrix Carrier

In order to demonstrate that the pharmaceutical agent is forming a complex with the matrix carrier, while protecting it from the external environment, two oral formulations with sensitive pharmaceutical agent such as proteins were tested. The tested pharmaceutical agents were DNase and Insulin. Composition of the DNase Formulation: (Packed in a Capsule)

| | |
|---|---|
| 50 g | DNase |
| 25 g | Silica |
| 80 g | Jojoba oil |
| 80 g | Oblepicha oil |
| 60 g | Olive oil |
| 90 g | Palm oil |
| 75 g | Amylopectin |
| 25 g | Beta-cyclodextrin |

Composition of the Insulin Formulation (Packed in a Capsule):

| | |
|---|---|
| 2 g | Insulin |
| 30 g | Silica R972 |
| 50 g | Beta-cyclodextrin |
| 200 g | Nutriose |
| 50 g | Maltsorb |
| 260 g | Olive oil |
| 260 g | Palm oil |
| 200 g | Oblepicha oil |

Methods:

Each capsule of the DNase Formulation was treated in 20 ml water at 35° C., for ~1 hour. The first sample was taken. 5 ml Hexane were added, and the mixture was mixed gently, and then centrifuged at 3000 RPM for 10 min. a second sample was taken. Then the mixture was mixed vigorously and centrifuged, and a third sample was taken. (and diluted by 5 folds). The DNase content was calculated from the peak area of DNase in the chromatogram against the calibration curve. The results are summarized in the table below.

TABLE 1

DNAse amount per capsule as calculated by HPLC method

| Calculated DNase weight (mg) | | | DNase peak area | | | |
|---|---|---|---|---|---|---|
| 3rd | 2nd | 1st | 3rd | 2nd | 1st | |
| 97.91 | 17.86 | 12.67 | 21460.3 | 19570.7 | 13890.1 | capsule 1 |
| 106.15 | 21.70 | 9.83 | 23265.4 | 23781.7 | 10767.7 | capsule 2 |
| 101.61 | 19.64 | 11.64 | 22269.8 | 21522.2 | 12752.8 | capsule 3 |
| 97.59 | 16.69 | 8.34 | 21389.1 | 18293.5 | 9134.4 | capsule 4 |
| 102.38 | 18.59 | 10.97 | 22439.1 | 20371.1 | 12025.6 | capsule 5 |
| 98.80 | 16.04 | 14.78 | 21653.8 | 17578.6 | 16194.6 | capsule 6 |
| 127.23 | 22.44 | 11.68 | 27886.5 | 24594.40 | 12797.7 | capsule 7 |
| 101.94 | 18.42 | 11.06 | 22343.3 | 20183.10 | 12122.1 | capsule 8 |
| 103.04 | 20.51 | 10.75 | 22584.8 | 22471.90 | 11783.9 | capsule 9 |
| 119.38 | 21.98 | 13.65 | 26165.80 | 24084.00 | 14955.4 | capsule 10 |
| 105.60 | 19.39 | 11.54 | | Av. | | |
| 9.85 | 2.24 | 1.84 | | SD | | |
| 9.33 | 11.55 | 15.99 | | RSD | | |

Further analysis shows that addition of 2.5% of surfactant (such as TWEEN 20), result in additional 8-10% increase in recovery of the DNase from the matrix carrier composition. Similar results were repeated for Insulin as a pharmaceutical agent in the matrix carrier composition formulation.

Furthermore, the Insulin formulation was tested by incubation with intestinal enzymes mix at 37° C. for various time lengths up to 16 hours. The results show no degradation of Insulin.

Additional experiments were performed for dissolution of the Insulin formulation by incubation at 37° C. in different mediums such as: pure water, saline, acidic solution with pepsine, fetal porcine serum and saline with 2.5% TWEEN 20. The matrix carrier decomposition was mainly observed in mediums that contain synthetic or natural blood surfactants such as, for example, Tween 20 or serum.

Example 8

Injection of Matrix Carrier Composition Comprising Insulin as Compared to Standard Insulin Injection The following Insulin formulations were used:
Formulation I—Standard Insulin Formulation
  Injection of insulin in PBS, 50 IU—Human recombinant Insulin in lyophilized form was dissolved in phosphate buffer at a concentration 50 IU/ml.
Formulation II—Matrix Carrier Composition
  The matrix carrier composition with Insulin formulation, 50 IU—The composition for the formulation is detailed in Example 7, above.
Experimental Details The study included 8 animals (rats) in each group.

Blood samples were withdrawn under halothan anesthesia from the rat tail. Blood glucose levels were measured from each blood samples by FreeStyle glucose meter, Abbott. After withdrawn, blood samples were kept in ice and then centrifuged at 3500 rpm, 4 C for plasma separation. Insulin level in rat plasma was measured by Human Insulin ELISA kit (Millipore kit (Cat. # EZHI-14K).

After the withdrawal of the first blood sample, rats were injected with Formulation I (insulin alone, 50 IU) or Formulation II (same Insulin within the matrix carrier composition, 50 IU). Additional blood samples were taken at time intervals after the injection: 3 hours, 6 hours, 9 hours, 12 hours and 24 hours.

Figure 2A:
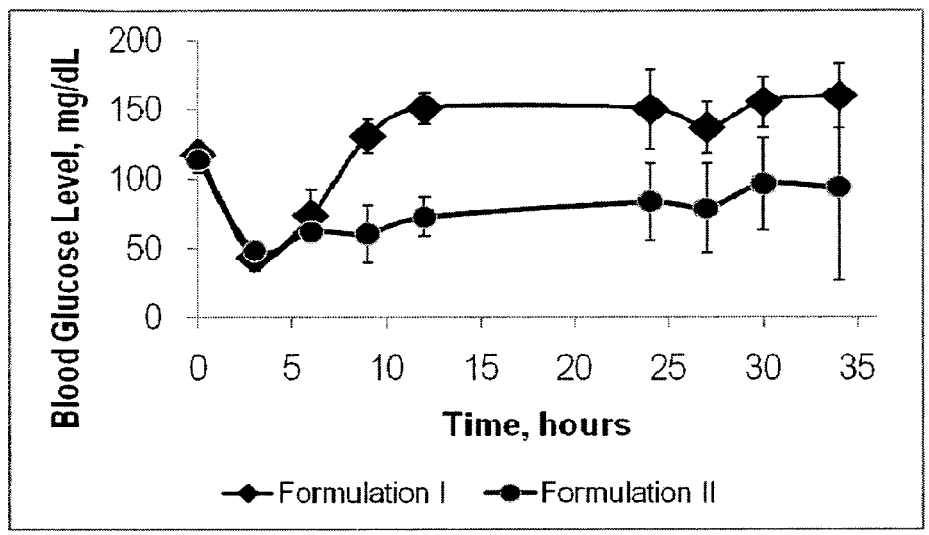
FIGS. 2A-B: Graphs depicting glucose levels (mg/dL) and the levels of insulin over time (hours) in blood of rats injected with various insulin formulations.
Figure 2B:
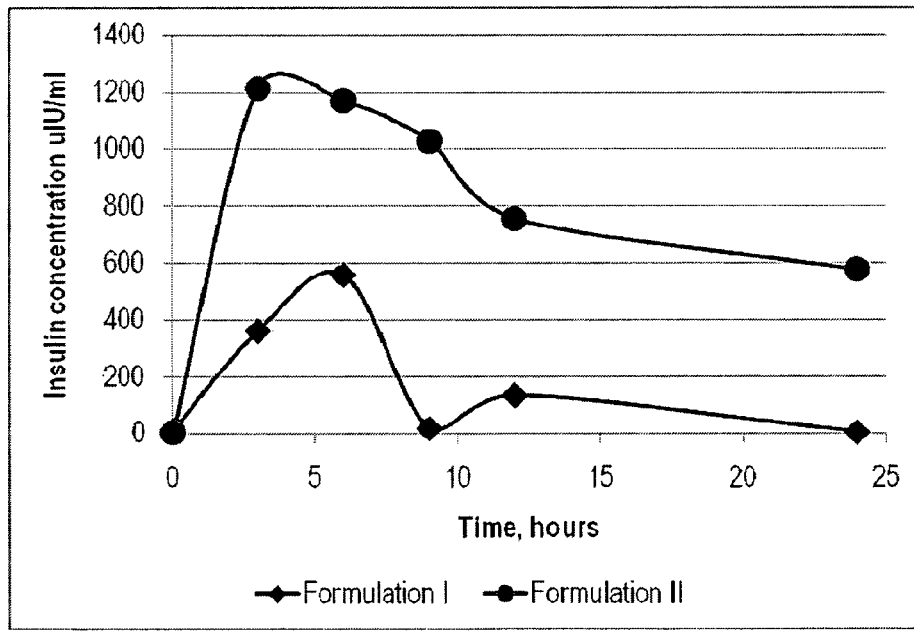

The results, illustrated in FIG. 2A show that blood glucose levels were reduced after injection of Formulation II, as compared to the standard insulin injection (Formulation I). In addition, the results illustrated in FIG. 2B show that plasma concentration of the injected human insulin in the rats (measured by Human Insulin ELISA Millipore kit (Cat. # EZHI-14K), is still high after 25 hours if the rats were injected with Formulation II, as compared to the standard insulin formulation injection (Formulation I).

The invention claimed is:

1. A matrix carrier composition for use in a pharmaceutical delivery system, the composition being a suspension of a particulate matter in a continuous oil phase, the particulate matter comprising an intermolecular association of at least:
   a first solid phase comprising nanoparticles having a hydrophobic surface, wherein the size of the nanoparticles is in the range of about 5-1000 nm;
   a second solid phase, comprising a biopolymer having hydrophilic and hydrophobic parts; and
   the continuous phase being associated with said first and said second solid phases,
wherein the weight of the biopolymer is at least twice that of the nanoparticles.

2. The matrix carrier composition of claim 1, wherein the matrix carrier composition does not include a surfactant.

3. The matrix carrier composition of claim 1, wherein the density of the first solid phase is higher than 1.4 g/cm$^3$.

4. The matrix carrier composition of claim 1, wherein the nanoparticles have a surface modified to be hydrophobic.

5. The matrix carrier composition of claim 1, wherein the nanoparticles are selected from the group consisting of silica nanoparticles, fumed silica nanoparticles, zinc oxide nanoparticles, carbon nanoparticles, titanium oxide nanoparticles and combinations thereof.

6. The matrix carrier composition of claim 1, wherein the biopolymer has a structure selected from linear, cyclic and branched biopolymer.

7. The matrix carrier composition of claim 1, wherein the biopolymer comprises a biopolymer selected from a saccharide and a polysaccharide.

8. The matrix carrier composition of claim 7, wherein the polysaccharide is selected from the group consisting of: starch, dextrin, cellulose, chitin, alpha glucan, beta glucan, amylopectin, glycogen, chitosan, cyclodextrin, mucopolysaccharide, and derivatives and combinations thereof.

9. The matrix carrier composition of claim 1, wherein the biopolymer comprises a structural protein selected from the group consisting of: a high molecular weight structural protein, a fibrous protein, a scleroprotein and combinations thereof.

10. The matrix carrier composition of claim 1, wherein the oil comprises an oil or a combination of oils selected from the group consisting of: naturally-occurring oils, synthetic oils, waxes and combinations thereof.

11. The matrix carrier composition of claim 1, wherein the oil comprises an oil or a combination of oils selected from a group consisting of:
   sesame oil, olive oil, linseed oil, evening primrose oil, silicone oil, sea buckthorn oil, palm oil, and combinations thereof;
   sunflower oil, corn oil, soybean oil, jojoba oil, marrow oil, grapeseed oil, hazelnut oil, apricot oil, macadamia oil, palm oil, almond oil, castor oil, and combinations thereof;
   oblepicha oil, jojoba oil, olive oil and combinations thereof;
   olive oil, linseed oil, oblepicha oil, sesame oil, palm oil and combinations thereof;
   jojoba oil, oblepicha oil, sesame oil, olive oil and combinations thereof;
   wax, jojoba oil, oblepicha oil, sesame oil, olive oil and combinations thereof; and
   linseed oil, oblepicha oil, olive oil, palm oil and combinations thereof.

12. The matrix carrier composition of claim 1, wherein the oil comprises lanolin, a fatty alcohol, a fatty acid ester or a phenylsilicone.

13. The matrix carrier composition of claim 1, further comprising an amino acid selected from the group consisting of: arginine, lysine, glutamic acid, aspartic acid and histidine and combinations and derivatives thereof.

14. The matrix carrier composition of claim 1, wherein said composition further comprises at least one agent selected from the group consisting of: an active pharmaceutical agent, nutritional agent, a targeting agent, an enhancer, an anti-oxidant, and combinations thereof.

15. The matrix carrier composition of claim 1, configured for topical administration.

16. The matrix carrier composition of claim 1, configured for parenteral administration.

17. A method of manufacturing the matrix carrier composition of claim 1, the method comprising:
   a. mixing a first solid phase with an oil, wherein the first solid phase comprises nanoparticles having a hydrophobic surface and particle size of about 5-1000 nm;
   b. activating a second solid phase, wherein the second solid phase comprises a biopolymer having hydrophilic and hydrophobic parts and wherein the weight of the biopolymer is at least twice that of the nanoparticles; and
   c. adding the activated second solid phase into an oil; and
   d. mixing the oil comprising the first solid phase and the oil comprising the activated second solid phase.

18. The method of claim 17, wherein activating comprises milling, vacuum treatment, chemical treatment, ultrasonic treatment or any combination thereof.

19. The method of claim 17, further comprising adding an agent selected from the group consisting of: a pharmaceutical agent, a nutritional agent, a targeting agent, an enhancer, an amino acid and combinations thereof optionally pre-mixed with an oil, into a) the oil comprising the activated second solid phase; b) the oil comprising the first solid phase; or c) a mixture of the oil comprising the activated second solid phase and the oil comprising the first solid phase.

* * * * *